United States Patent
Edelhauser et al.

(10) Patent No.: US 9,044,271 B2
(45) Date of Patent: Jun. 2, 2015

(54) EXTERNAL FIXATION SYSTEM

(71) Applicant: Stryker Trauma SA, Selzach (CH)

(72) Inventors: Adam John Edelhauser, Nyack, NY (US); Richard J. Tomasheski, Wayne, NJ (US)

(73) Assignee: Stryker Trauma SA (CH)

( * ) Notice: Subject to any disclaimer, the term of this patent is extended or adjusted under 35 U.S.C. 154(b) by 157 days.

(21) Appl. No.: 13/621,335

(22) Filed: Sep. 17, 2012

(65) Prior Publication Data

US 2013/0018374 A1 Jan. 17, 2013

Related U.S. Application Data

(62) Division of application No. 12/661,015, filed on Mar. 9, 2010, now Pat. No. 8,333,766.

(60) Provisional application No. 61/209,677, filed on Mar. 10, 2009.

(51) Int. Cl.
- *A61F 5/04* (2006.01)
- *A61B 17/62* (2006.01)
- *A61B 17/66* (2006.01)
- *A61B 19/00* (2006.01)

(52) U.S. Cl.
CPC .................. *A61B 17/62* (2013.01); *A61B 17/66* (2013.01); *A61B 2019/461* (2013.01)

(58) Field of Classification Search
CPC ....................................................... A61B 17/62
USPC ...................................................... 606/54–59
See application file for complete search history.

(56) References Cited

U.S. PATENT DOCUMENTS

| | | | |
|---|---|---|---|
| 3,977,397 A | 8/1976 | Kalnberz et al. | |
| 4,365,624 A | 12/1982 | Jaquet | |

(Continued)

FOREIGN PATENT DOCUMENTS

| | | |
|---|---|---|
| DE | 202006006734 U1 | 6/2006 |
| FR | 2576774 A1 | 8/1986 |

(Continued)

OTHER PUBLICATIONS

Alizade et al., Mech. Mach. Theory, vol. 29, No. 1, pp. 115-124, 1994, Great Britain.

(Continued)

*Primary Examiner* — Ellen C Hammond
(74) *Attorney, Agent, or Firm* — Lerner, David, Littenberg, Krumholz & Mentlik, LLP

(57) ABSTRACT

An external fixation system comprising: first and second planar at least part-circular ring elements, the first ring element having a circumferential track extending along the part-circular circumference thereof; a plurality of struts each having a first and second end, the first end of each strut coupled to the first ring by a first connector and the second end of each strut coupled to a second ring by a second connector, the first connector including a spherical joint; the second connector non-rotatably coupled to the second ring, the strut second end being coupled to the second connector by a U-joint; shuttles mounted on the track of the first ring for movement there along with one shuttle coupled to each strut; and means for controlling the angular position of each strut second end and means for controlling the position of each shuttle along the circumferential track on the first ring.

25 Claims, 32 Drawing Sheets

(56) References Cited

U.S. PATENT DOCUMENTS

| | | |
|---|---|---|
| 4,554,915 A | 11/1985 | Brumfield |
| 4,615,338 A | 10/1986 | Ilizarov et al. |
| 4,768,524 A | 9/1988 | Hardy |
| 4,784,125 A * | 11/1988 | Monticelli et al. ............ 606/56 |
| 4,819,496 A | 4/1989 | Shelef |
| 4,889,111 A | 12/1989 | Ben-Dov |
| 4,976,582 A | 12/1990 | Clavel et al. |
| 4,978,348 A | 12/1990 | Ilizarov et al. |
| 5,028,180 A | 7/1991 | Sheldon et al. |
| 5,087,258 A | 2/1992 | Schewior |
| 5,122,140 A | 6/1992 | Asche et al. |
| 5,179,525 A | 1/1993 | Griffis et al. |
| 5,279,176 A | 1/1994 | Tahmasebi et al. |
| 5,301,566 A | 4/1994 | Tahmasebi et al. |
| 5,358,504 A | 10/1994 | Paley et al. |
| 5,372,597 A | 12/1994 | Hotchkiss et al. |
| 5,397,322 A | 3/1995 | Campopiano et al. |
| 5,568,993 A | 10/1996 | Potzick |
| 5,702,389 A | 12/1997 | Taylor et al. |
| 5,709,681 A | 1/1998 | Pennig |
| 5,728,095 A | 3/1998 | Taylor et al. |
| 5,870,834 A | 2/1999 | Sheldon |
| 5,891,143 A | 4/1999 | Taylor et al. |
| 5,971,984 A | 10/1999 | Taylor et al. |
| 6,021,579 A | 2/2000 | Schimmels et al. |
| 6,030,386 A | 2/2000 | Taylor et al. |
| 6,086,283 A | 7/2000 | Ziegert |
| 6,099,217 A | 8/2000 | Wiegand et al. |
| 6,129,727 A | 10/2000 | Austin et al. |
| 6,196,081 B1 | 3/2001 | Yau |
| 6,277,118 B1 | 8/2001 | Grant et al. |
| 6,355,037 B1 | 3/2002 | Crosslin et al. |
| 6,428,540 B1 | 8/2002 | Claes et al. |
| 6,648,583 B1 | 11/2003 | Roy et al. |
| 6,671,975 B2 | 1/2004 | Hennessey |
| 6,701,174 B1 | 3/2004 | Krause et al. |
| 6,769,194 B2 | 8/2004 | Hennessey |
| 7,127,660 B2 | 10/2006 | Blaum |
| 7,282,052 B2 | 10/2007 | Mullaney |
| 7,422,593 B2 | 9/2008 | Cresina et al. |
| RE40,914 E | 9/2009 | Taylor et al. |
| 8,257,353 B2 | 9/2012 | Wong et al. |
| 2002/0010465 A1 | 1/2002 | Koo et al. |
| 2005/0015087 A1 | 1/2005 | Walulik et al. |
| 2005/0215997 A1 | 9/2005 | Austin et al. |
| 2005/0251136 A1 | 11/2005 | Noon et al. |
| 2006/0184169 A1 | 8/2006 | Stevens |
| 2007/0055234 A1 | 3/2007 | McGrath et al. |
| 2007/0161984 A1 | 7/2007 | Cresina et al. |
| 2007/0250071 A1 | 10/2007 | Soerensen et al. |
| 2008/0021451 A1 | 1/2008 | Coull et al. |
| 2010/0087819 A1 | 4/2010 | Mullaney |

FOREIGN PATENT DOCUMENTS

| | | |
|---|---|---|
| FR | 2756025 A1 | 5/1998 |
| WO | 9418898 | 9/1994 |
| WO | 01/15611 A1 | 3/2001 |
| WO | 03/086213 | 10/2003 |

OTHER PUBLICATIONS

Basic Ilizarov Techniques, Techniques in Orthopaedics, vol. 5, No. 4, pp. 55-59, Dec. 1990.

European Search Report, EP 08 15 0960, Jul. 2008.

Hwang et al., Asian Journal of Control, vol. 6, No. 1, pp. 136-144, Mar. 2004.

International Search Report and Written Opinion, PCT/US2010/000712, dated Jun. 28, 2010.

Nanua et al., IEEE Transactions on Robotics and Automation, vol. 6, No. 4, pp. 438-444, Aug. 1990.

S.V. Sreenivasan et al., "Closed-Form Direct Displacement Analysis of a 6-6 Stewart Platform," Mech. Mach. Theory, vol. 29, No. 6, pp. 855-864, 1994.

Smith&Nephew, Taylor Spatial Frame, website printout, Aug. 12, 2009.

TSAI, Technical Research Report, The Jacobian Analysis of a Parallel Manipulator Using Reciprocal Screws, T.R. 98-34, 1998.

U.S. Appl. No. 09/827,252 (not yet published), 2009.

* cited by examiner

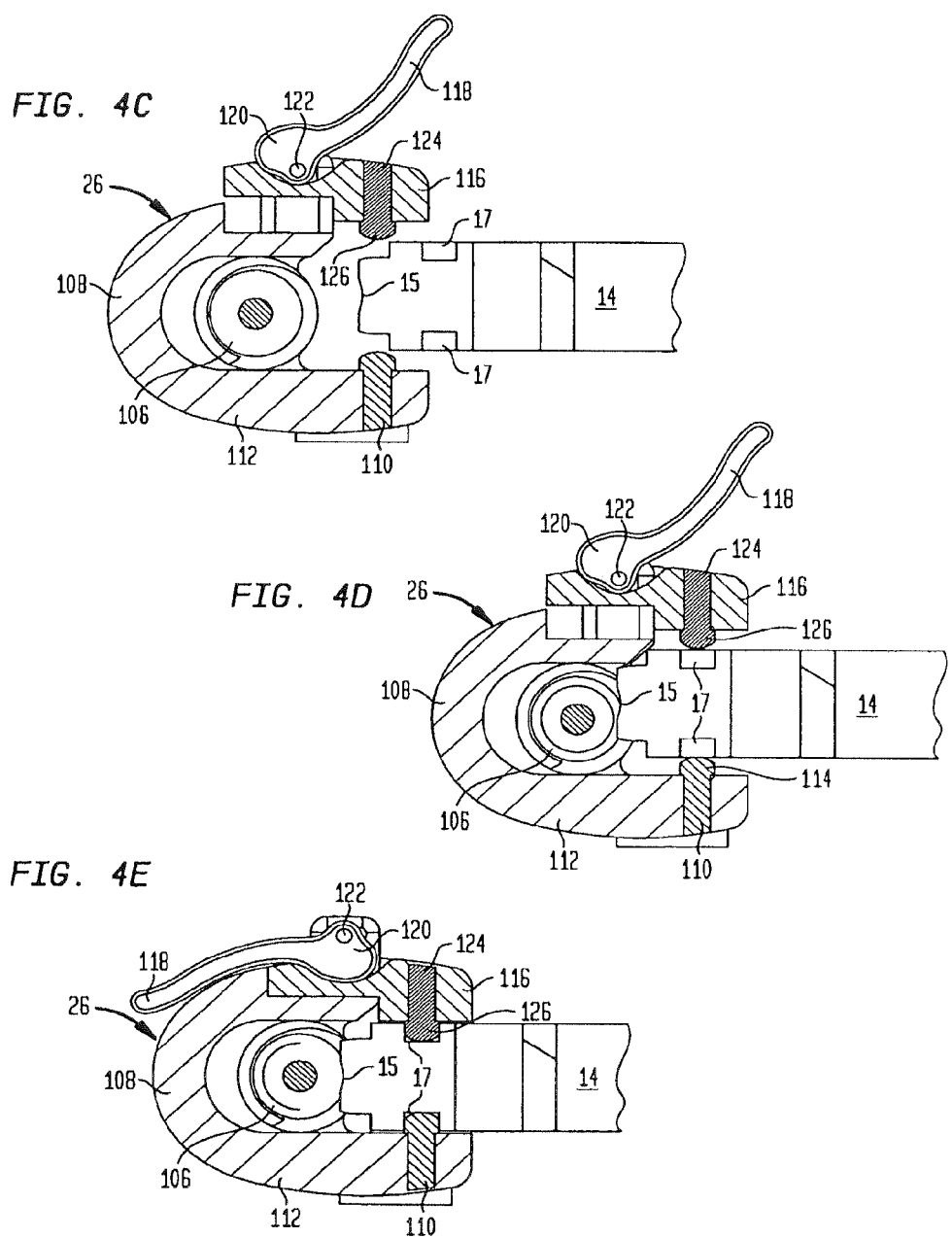

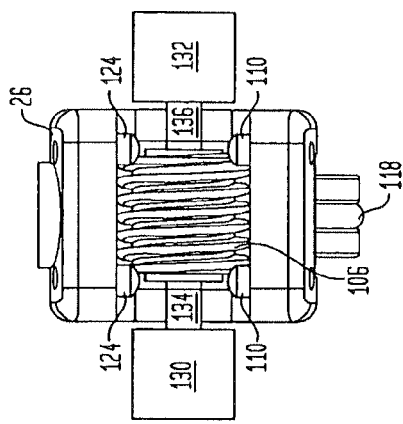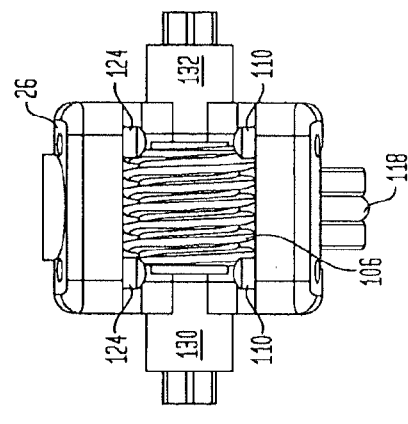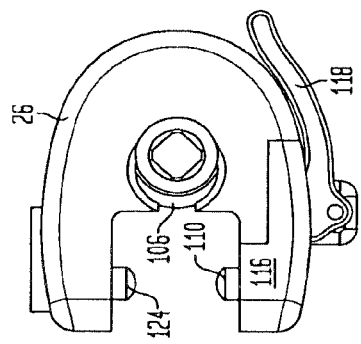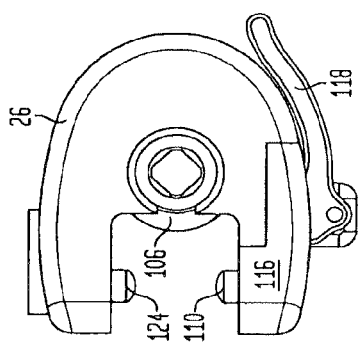

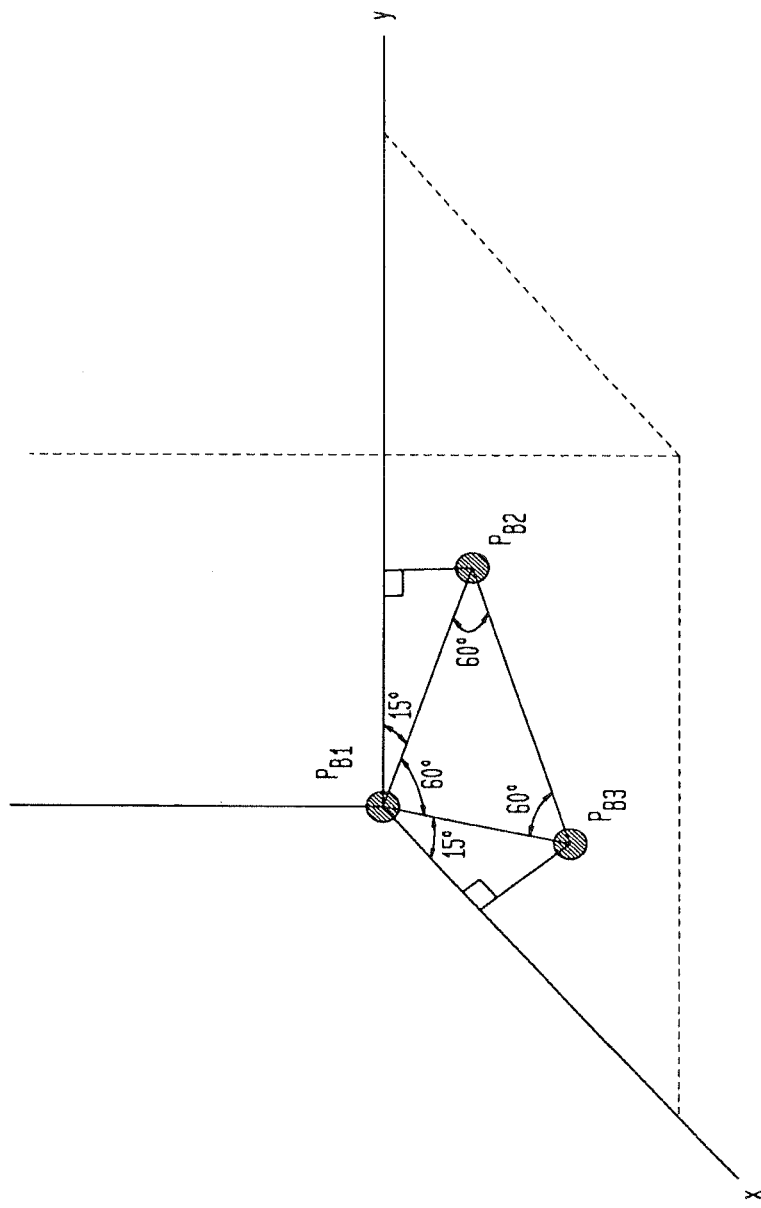

FIG. 9
FIG. 10
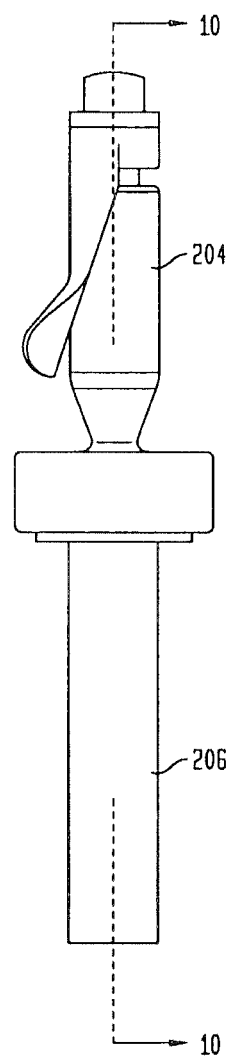
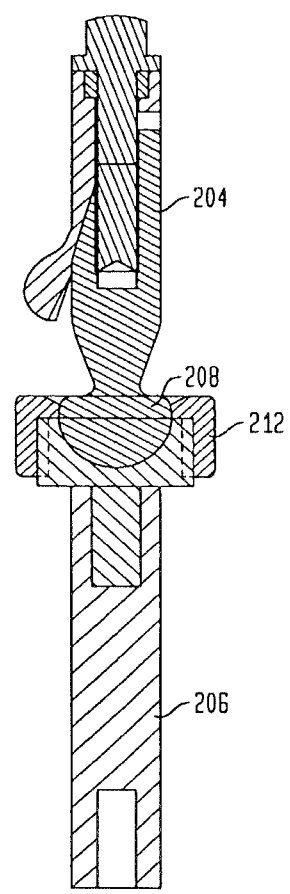

EXTERNAL FIXATION SYSTEM

CROSS-REFERENCE TO RELATED APPLICATION

This application is a divisional of U.S. patent application Ser. No. 12/661,015, filed on Mar. 9, 2010, now U.S. Pat. No. 8,333,766 which claims the benefit of the filing date of U.S. Provisional Patent Application No. 61/209,677 filed Mar. 10, 2009, the entire disclosures of which are hereby incorporated herein by reference.

BACKGROUND OF THE INVENTION

The external fixation market can be divided into two major segments: acute trauma and reconstructive. The customers, products, and needs of each segment are distinctly different. The trauma segment is dominated by modular fixators. These frames are characterized by limited componentry and very rapid application. Consequently, they are known for being fairly simple products. Most of these frames are used for temporizing fixation and quite often are only on the patient for hours or days.

The reconstructive segment leans heavily toward ring fixation, but unilateral frames also enjoy an appreciable market share. Ring fixators such as the well known Ilizarov frame are by far the most stable and capable of external fixators. Such frames are shown in U.S. Pat. Nos. 4,365,624; 4,615,338; 4,978,348; 5,702,389; and 5,971,984. Their use of a combination of pins and wires to achieve a variety of polyaxial pin/wire attachments creates this stability. They can accomplish a full six axes of deformity correction and, when applied and managed well, can correct primary deformities while not creating secondary deformities. Rotational deformities are the sole domain of the ring fixator. However, mastery of the techniques and the products themselves is a long and daunting process that it is not attractive to many users.

The present invention relates to a method for using an improved orthopaedic external fixator including a mechanism that allows two bone elements or portions to be fixed relative to one another while allowing complete repositioning of the two bone elements or portions relative to one another.

It is often necessary to realign, reposition and/or securely hold two bone elements relative to one another. For example, in the practice of medicine, bone fragments and the like must sometimes be aligned or realigned and repositioned to restore boney continuity and skeletal function. At times, this may be accomplished by sudden maneuver, usually followed by skeletal stabilization with cast, plate and screws, intramedullary devices, or external skeletal fixators.

A bone fragment can be moved, in general, from its original position as in a nonunion or malunion or from its intended position as in congenital deformities along six separate axes, a combination of three orthogonal translational axes (e.g., typical "X," "Y" and "Z" axes) and three orthogonal rotational axes (e.g., rotation about such typical "X," "Y" and "Z" axes).

External fixation devices are attached to the boney skeleton with threaded and/or smooth pins and/or threaded and/or smooth and/or beaded wires. Such constructs are commonly referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

A circumferential external fixator system was disclosed by G. A. Ilizarov during the early 1950s. The Ilizarov system includes at least two rings or "halos" that encircle a patient's body member (e.g., a patient's leg), connecting rods extending between the two rings, transfixion pins that extend through the patient's boney structure, and connectors for connecting the transfixion pins to the rings. Use of the Ilizarov system to deal with angulation, translation and rotation is disclosed in "Basic Ilizarov Techniques," *Techniques in Orthopaedics®*, Vol. 5, No. 4, December 1990, pp. 55-59.

Prior art orthopaedic external fixators differ in their ability to move or adjust one bone fragment with respect to the other in a gradual fashion. Some allow gradual translation, others allow gradual rotation about two axes. The Ilizarov system can provide an external fixation device that could provide gradual correction along and about six axes; however, such a device would require many parts and would be relatively complicated to build and use in a clinical situation.

Often orthopaedic external fixators such as Ilizarov fixators must be repositioned after their initial application. Such modification may be necessary to convert from one correctional axis to another or to convert from an initial adjustment type of fixator to a weight bearing type of fixator, some of the correctional configurations not being stable enough for weight bearing.

A "Steward platform" is a fully parallel mechanism used in flight and automotive simulators, robotic end-effectors, and other applications requiring spatial mechanisms with high structural stiffness and includes a base platform, a top platform, and six variable limbs extending between the base and top platforms. See S. V. Sreenivasan et al., "Closed-Form Direct Displacement Analysis of a 6-6 Stewart Platform," *Mech. Mach. Theory*, Vol. 29, No. 6, pp. 855-864, 1994.

Taylor et al. U.S. Pat. No. 5,702,389 relates to a fixator that can be adjusted in six axes by changing strut lengths only, without requiring joints to be unclamped, etc. This patent includes a first ring member or swash plate for attachment relative to a first bone element; a second ring member or swash plate for attachment relative to a second bone element. Six adjustable length struts having first ends movably attached to the first member and second ends movably attached to the second member are provided. The first ends of the first and second struts are joined relative to one another so that movement of the first end of one of the first and second struts will cause a corresponding movement of the first end of the other strut, with the first ends of the third and fourth struts joined relative to one another so that movement of the first end of one of the third and fourth struts will cause a corresponding movement of the first end of the other strut. The third and fourth struts and fifth and sixth struts are similarly joined. Second ends of the first and sixth struts joined relative to one another so that movement of the second end of one of the first and sixth struts will cause a corresponding movement of the second end of the other strut. Second ends of the second and third struts and fourth and fifth struts are formed in a similar manner. Thus, changing the length of the struts effects reposition of the bone segments.

BRIEF SUMMARY OF THE INVENTION

A parallel robot is defined as a manipulator consisting of a fixed base and an end-effector with 6 degrees of freedom (DOF) that are linked together by at least two independent kinematic chains. Actuation of such a device takes place through 6 simple actuators. It is important to note that the number of actuators is equal to the number of degrees of freedom; a 6 DOF robot will require six actuators. Furthermore, each connecting chain must also have 6 degrees of freedom. Each DOF comes from a joint connecting two rigid bodies within the chain. The most commonly used joints in parallel robots are revolute (R), prismatic (P), universal (U), and spherical (S). R and P joints each grant one DOF, U joints grant two, and S joints give three. Universal joints consist of two revolute joints whose axes of rotation intersect, and are sometimes treated as two joints instead of one.

The general nomenclature for describing a parallel robot's configuration is to list the number of struts followed by the joint setup, with actuated joints underlined. Our present device is of a 3-USR (or 3-RRSR) configuration. The Base Adjustment Unit (BAU) is a modified U-joint; one of the axes of rotation is controlled through the worm-gear interface, and the other is free. The strut connects the BAU to the sliding unit via a free spherical joint, and the sliding unit revolves around the upper ring by another worm-gear interface. This leads to a kinematic chain with 2 DOF×3 chains=6 DOF.

The design shown in provisional application No. 61/209,677 filed Mar. 10, 2009 has 6 DOF while using only three struts. However, it has an alternate joint configuration. The BAU was connected to the second ring via an assembly that allowed it to freely swivel, and the strut's connection to the sliding unit was via free universal joint instead of a spherical joint. This led to a 3-RUUR (or 3-RRRRRR) configuration. Again, both configurations satisfy the necessary conditions to be considered a parallel robot.

The proximal U-joints of provisional application No. 61/209,677 are replaced with a ball and socket (or spherical joint) and the base adjustment unit (BAU) is no longer free to spin about the axis that connects it to the second ring.

An embodiment of the presently disclosed external fixation system has first and second planar at least part-circular ring elements. The centers of the first and second ring elements are spaced along an axis. The first ring element has a circumferential track extending along the part-circular circumference thereof. Three variable length struts each having first and second ends are provided. The variable length struts can be locked at a desired length after the initial positioning of the ring element. The first end of each strut is coupled by a first connector to the first ring and the second end of each strut is coupled to a second ring by a second connector. The second connector strut is fixedly coupled to the second ring in a manner which prevents rotation of the connector about an axis perpendicular to the plane of the second ring. The second connector has a U-joint having a first axis allowing for rotation in a plane parallel to the plane of the second ring. The U-joint has a second axis allowing rotation about the first axis. Three shuttles are mounted on the track of the first ring for movement there along with one shuttle coupled to the first end of each strut via the first connector. Means are provided for controlling the rotational and angular position of each strut second end and means for controlling the position of each shuttle along the circumferential track on the first ring.

The first and second rings may be complete or half circles or may be other geometric shapes, such as square or rectangular. The shuttle connected to the strut first ends may be spaced 120° around a circumference of the first ring. However, the three shuttles mounted on the first ring are movable and can move along an arc limited only by the position of the adjacent shuttle. Thus, the first ends of the three struts may move through a large portion of the first ring circumference.

Preferably, each shuttle or sliding unit can move along the track on the first ring in, for example, one to five degree increments and the angular location of the strut second end with respect to the second ring may be in five to ten degree increments. In this case, there would be between 36 and 72 holes spaced equally around the lower ring for mounting the second connector. The angular movement of the shuttle with respect to the first ring can also be infinitely variable.

Each strut first end has a connector with a spherical joint coupling the strut to the shuttle mounted on the first ring and a connector with a standard U-joint coupling each strut second end to the second ring. The U-joint has a drive system controlling the movement of the joint about one axis of the U-joint. Preferably, the drive axis is parallel to the plane of the second ring. The drive system preferably comprises a computer controlled stepper or servo motor and a gear drive system.

The external fixation system has first and second ring elements the first ring having three shuttles mounted on the ring element for controlled movement about a circumference of the ring. There are three connectors fixed to the second ring with three struts having first ends connected to a respective shuttle by connectors having a spherical or ball joint and a second end connected to a respective connector on the second ring by a standard U-joint rotatable about a first and second axis and rotatable in a controlled manner about the second axis which is perpendicular to the first axis. The first axis preferably extends parallel to the plane of the ring and the connector is fixed on the ring in a manner to prevent its rotation about the mounting hole axis. A programmable or microprocessor controller is provided for controlling the movement of the shuttle about the circumference of the first ring and for controlling the movement of the strut second end about the first axis of the connector on the second ring. This can also be adjusted manually.

An embodiment of the presently disclosed external fixation system incorporates three variable length struts that can be adjusted in length and then locked. Once locked the struts can manipulate the relative position of bone fragments to one another. The system is capable of moving in six degrees of freedom (DOF). For movement, it will incorporate either the calibration device disclosed in U.S. Pat. No. 6,017,534, the entire disclosure of which is incorporated herein by reference, or six dedicated servo or stepper motors respectively coupled to the shuttles and second ends of each strut. The calibration device or servo/stepper motors are controlled by software. The software is the interface the surgeon or user will use to determine the daily adjustments of the frame assembly. The system incorporates position sensors such as potentiometers and/or optical encoders and/or other position sensors at the moving points along the frame to not only determine the initial position, for software input/setup, but also to provide feedback to insure that the daily adjustments are being made properly.

An embodiment of the presently disclosed external fixation system has two rings and three fixable length struts having a spherical joints on a first connector on the first ring and a standard U-joints having two axes of rotation. The U-joint has a first of the two axes of rotation controlled (cannot move freely) by a worm and worm gear. The other axis of the second connector moves freely about an axis perpendicular to the first axis.

The movement of the fixed strut about the first axis and third axis is free moving. The movement about the second axis is controlled by the interaction of the worm gear and a worm situated on the second ring which worm extend parallel to the worm gear.

The driving connection of the worm to the "smart tool" described in U.S. Pat. No. 6,017,354 or servo/stepper motor will be a miter and bevel connection (where the worm has a bevel gear at one end and the tool/motor has a miter gear at its respective end). This relationship will allow the motor's miter gear to drive the worm's bevel gear which in turn drives the worm to the worm gear. This action controls one of the axes of rotation that affects its respective strut's angle (relative to the second ring).

The first connector couples the struts to the first ring by a sliding shuttle unit, which glides along two circumferential grooves on either side of the first ring. The grooves are spaced radially inwardly the toothed outer circumferential surface of the first ring. The movement of the sliding unit is controlled by the interaction of worm gear teeth (on the outside of the first ring) and a worm. Each sliding unit can be moved about the circumference of the moving ring independently. The worm is to be driven by a "smart tool" or a dedicated stepper/servo motor or a hand tool. The driving connection of the worm to the tool or motor is preferably a miter and bevel gear connection where the worm has a bevel gear at one end and the smart tool/motor has a miter gear at its respective end. Any gear box and motor could be used to drive the sliding units.

With six points of adjustment, the system will have complete control (in six axes of rotation) over the relative position of the two rings without changing strut length.

In an alternate embodiment, the external fixation system includes a first platform, a second platform, and a plurality of non-prismatic kinematic chains. By "non-prismatic," it is meant that the kinematic chain links do not extend in length during actuation. Each kinematic chain connects the first platform to the second platform and includes at least two actuated joints. At least one actuated joints is configured to move along a perimeter of the first platform. This embodiment further includes a means for actuating the actuated joints.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

While the system has been described for use in an external fixation ring system the identical structures and principles could be used in any application where platforms are manipulated such as a Stewart platform.

BRIEF DESCRIPTION OF THE DRAWINGS

FIG. 4C through FIG. 4E are sequential views of the mounting of the shuttle or sliding unit of the present invention on the upper ring shown in FIG. 4A;

FIG. 4G through FIG. 4J show the worm drive contained in shuttle or sliding unit in a disengaged position and an engaged position with the teeth on the outer circumference of the ring of FIG. 4A;

FIG. 5 is a depiction of an x, y, z coordinate system including various points of the second ring where struts are attached thereto;

FIG. 9 is an elevation view of a first strut portion and a ring connector of the alternate embodiment of the present invention;

FIG. 10 is a cross-sectional view of the strut element of FIG. 9 along lines 10-10;

DETAILED DESCRIPTION

Figure 1:
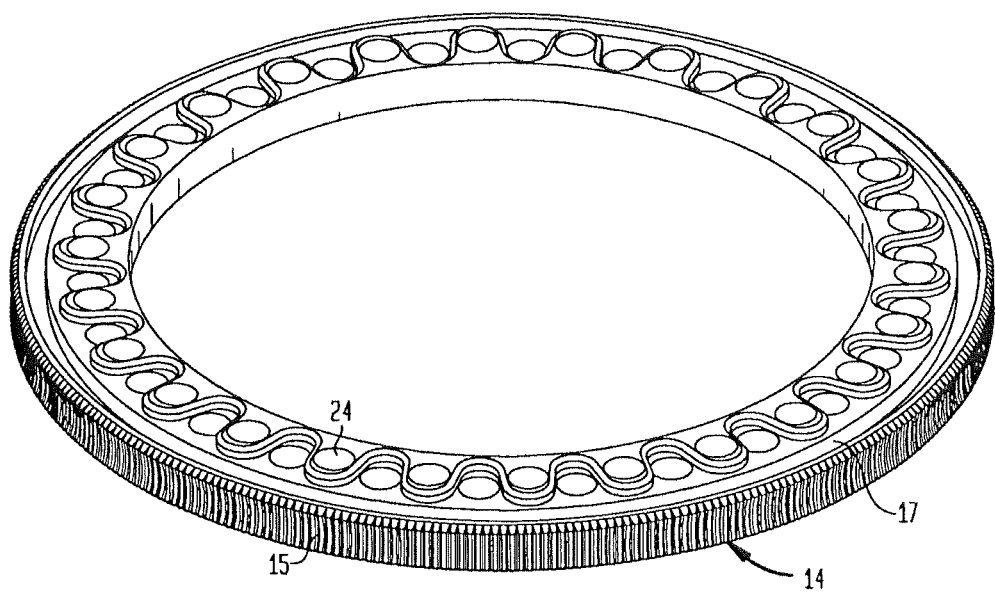
FIG. 1 is an isometric view of the external fixation ring used in the external fixation system of the present invention.
Figure 2:
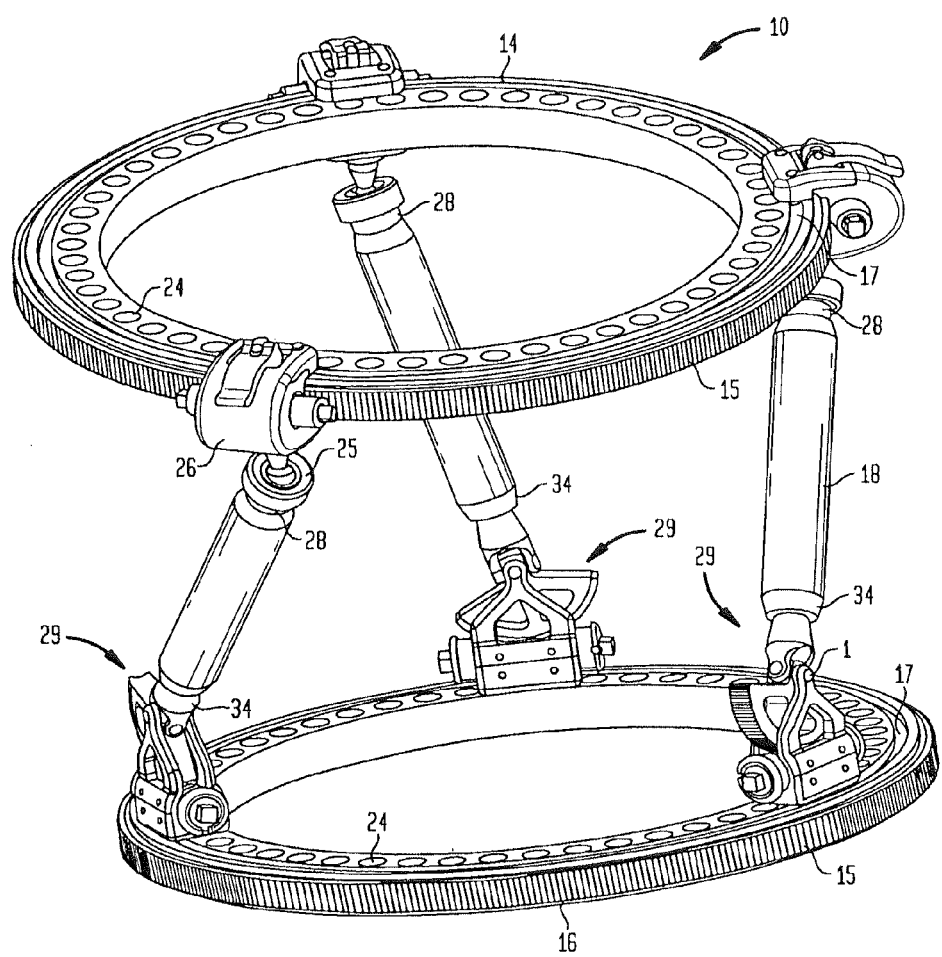
FIG. 2 is an isometric view of a pair of rings shown connected by three struts.

Referring to FIGS. 1 and 2, there is shown the external fixation system of the present invention generally denoted as 10. The external fixation system 10 may be utilized with any long bone, in particular, the tibia and the femur.

As shown in FIGS. 1 and 2, the external fixation system 10 includes a first ring 14 and a second ring 16. In some embodiments, both rings 14, 16 are identical. Each ring 14 includes a worm gear 15 formed around its outer circumference. Two grooves 17 are formed in the upper and lower surfaces of ring 14 around its circumference adjacent the worm gear 15. As shown in FIG. 1, ring 14 (or 16) may include a multi-level configuration with the upper and lower surfaces having alternate steps including through holes 24. Such an external fixation ring (without the circumferential worm gear) is described in U.S. patent application Ser. No. 12/157,612 filed Jun. 11, 2008, the entire disclosure of which is incorporated herein by reference. In certain embodiments, rings 14, 16 are connected by three variable length struts 18. The three struts 18 have first ends 28 mounted to the first ring 14 via a connector 25 coupled to a sliding or shuttle unit 26, which is circumferentially moveable around ring 14 as described below. In several embodiments, the first ends 28 are connected to sliding units or connector 26 by a connector 25 having a ball or spherical joint. As is typical, the rings are connected to tibia 12 by a plurality of bone pins or wires (not shown). In some embodiments, the pins or wires are connected to each ring 14, 16 by connection elements, which are located in one or more of a multiplicity of holes 24 around the circumference of the first and second rings 14 and 16. Although holes 24 are shown, any structure which locates the pins or wires with respect to the circumference of rings 14 and 16 can be utilized. Lower ends 34 of struts 18 are connected to lower ring 16 by standard universal-joints 35, which allow free rotation about only two axes rather than the three axes of the spherical joint at the first strut end 28.

Ring 14 may be coupled to a first bone element via pins or wires and, similarly, ring 16 is coupled to a second bone element by similar pins or wires. Shuttle unit 26 is slidable about ring 14 in a track and is preferably driven by a servo motor. A second connector 29 between strut 18 and second lower ring 16 has a standard universal joint 35, which allows the strut to rotate freely about first and second axes A and B (see FIG. 3A). First axis A is oriented perpendicular with respect to second axis B. The universal joint 35 may also be powered by servo motors independently connected to a gear rotatable about a pivot pin axially oriented along axis A of universal joint 35. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon. In addition, the movement can be programmed into a computer means, which can automatically increment movement, for example, on a daily basis. Strut 18 is of variable length but can be locked at a desired length after the surgeon initially sets the starting location of the system.

Figure 3A:
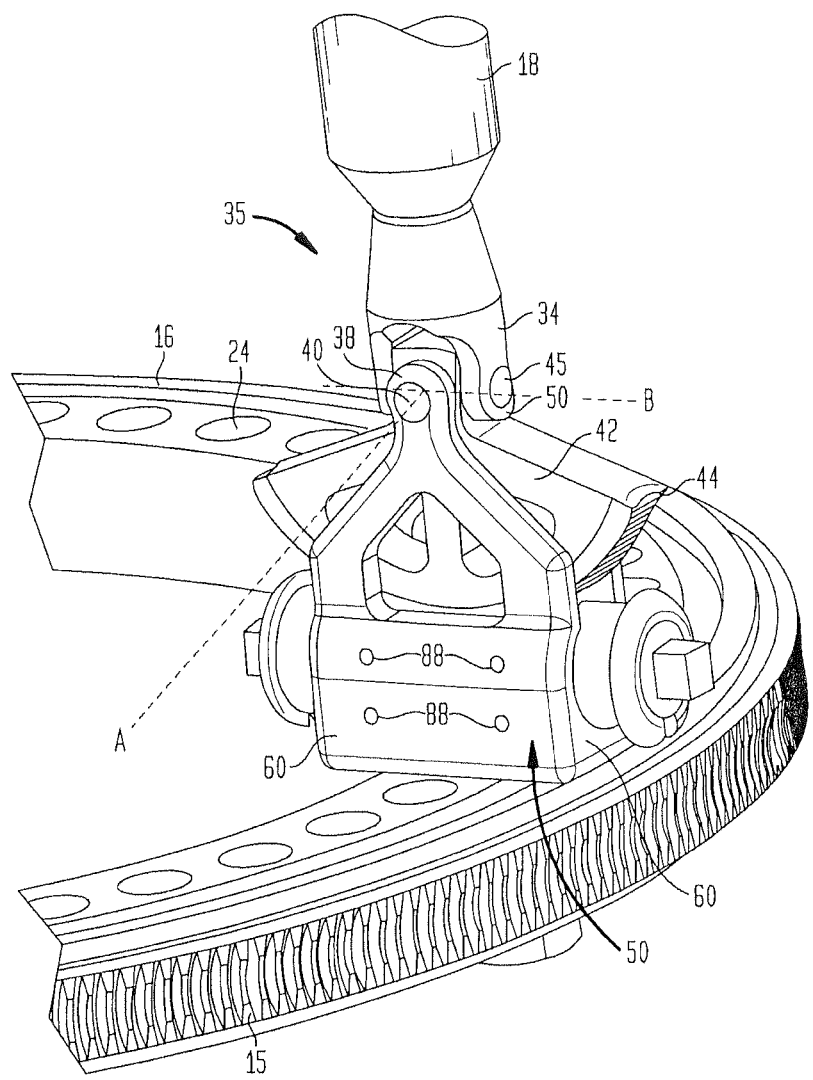
FIG. 3A is an isometric view of an actuated joint connected to the ring.
Figure 3B:
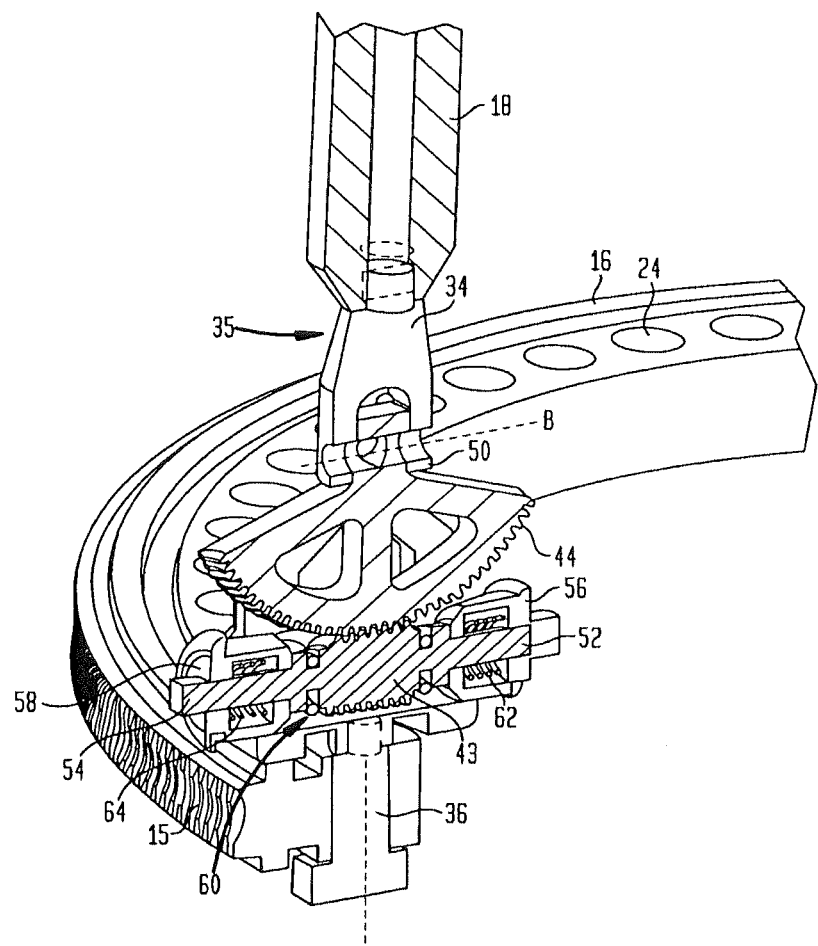
FIG. 3B is an isometric cross-sectional view of the actuated joint connected to the ring.

Referring to FIGS. 3A and 3B, there is shown universal joint 35 coupling a second end 34 of rod 18 to the second ring 16. Preferably, end 34 is bifurcated and has a bore for receiving a pivot pin. A connector 36 is non-rotatably connected to second ring 16 through one of the multiplicity of through holes 24 therein. Connector 36 includes a pair of bushings 38 through which a pivot pin 40 is received for rotation about axis A. Pivot pin 40 is driven by a gear portion or worm gear 42 which, in one embodiment, it is integral therewith. In the preferred embodiment, gear portion 42 is driven by a servo motor having a gear system with a drive connector or worm 43 for engaging gear teeth 44 of gear portion 42. Pin 40 has a bore therethrough for receiving a pin 45 pivotably coupling end of shaft or rod 18 thereto for rotation about axis B. The bore in pin 40 receives pin 45, which is mounted on a pair of bushings 50 on bifurcated end portion 34. Referring to FIG. 3B, a housing 60 is shown in which the miter gear 43 is retractably mounted. Miter gear 43 is mounted on shafts 52 and 54, which in turn are received within spring-loaded mounting elements 56 and 58. Housing 60 has a cylindrical outer wall 60 as best seen in FIG. 3A. Mounting elements 56 and 58 are biased inwardly by springs 62 and 64, which forces miter gear 43 into engagement with the teeth 44 of gear portion 42. When a user moves mounting elements 56 and 58 actually outwardly along shafts 52 and 54, respectively, against the forces of springs 62 and 64, miter gear 43 can move downwardly in FIGS. 3A and 3B out of engagement with teeth 44. Springs 62 and 64 then lock the mounting elements 56 and 58 in this position so that shaft 18 may be freely pivoted about axis A of FIG. 3A.

Figure 3C:
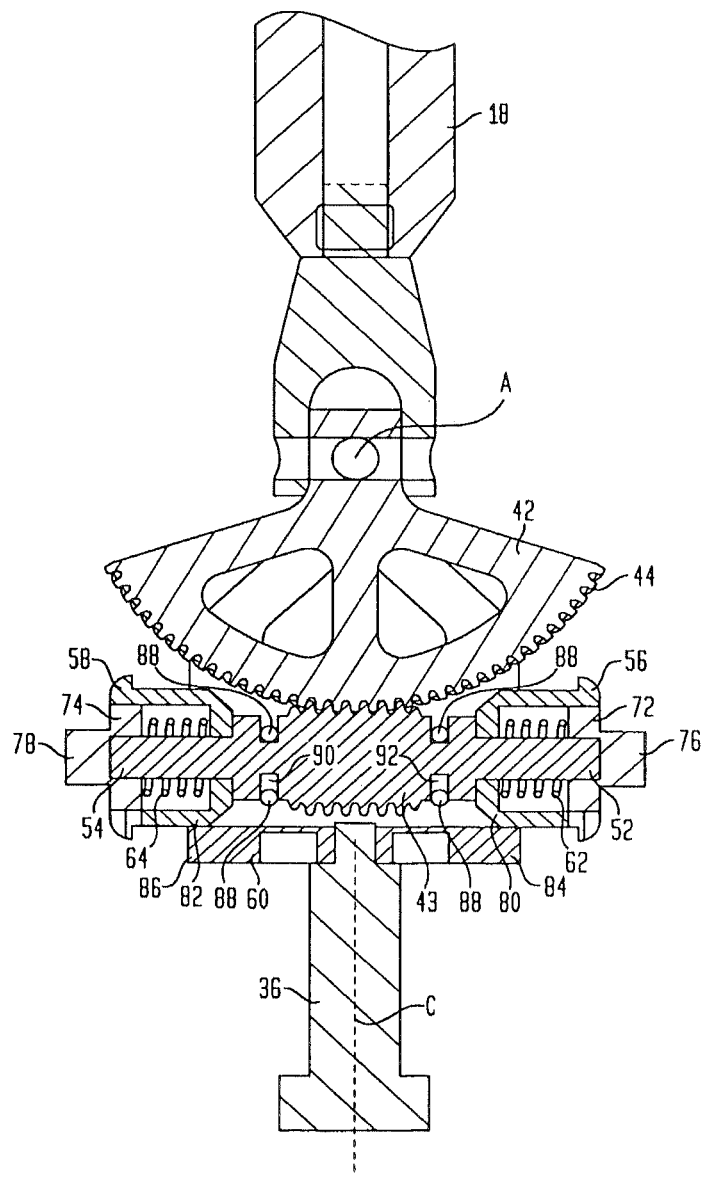
FIG. 3C is an elevation cross-sectional view of the actuated joint connected to the ring.

Referring to FIG. 3C, there is shown a cross-sectional elevation view of the connector of FIGS. 3A and 3B. This figure is useful for showing the disengagement of worm 43 from teeth 44 of worm gear 42. Mounting elements 56 and 58 are slidably mounted on circular end plates 72 and 74, respectively. End plates 72 and 74 are fixably coupled to drive sockets 76, 78, which in turn are integrally connected with ends 52 and 54 of worm 43. Thus, when a drive tool is attached to either drive element 76 or 78 and rotated, worm 43 will rotate and will engage with teeth 44, rotating worm gear 42 about axis A. This can also be accomplished via a servo motor.

In order to disengage worm 43 from teeth 44, mounting elements 56 and 58 are moved outwardly, thereby compressing springs 62 and 64 until chamfers 80 and 82 engage ends 84 and 86 of the housing 60. At this point, worm 43 can move downwardly in FIG. 3C and out of engagement with teeth 44 of worm gear 42. In order to ensure that worm 43 maintains its central location within housing 60, four pins 88 are mounted on housing 60, as shown in FIG. 3A, and engage in the circumferential grooves 90 and 92 in worm 43. Grooves 90 and 92 have sufficient depth to allow worm 43 to be moved into and out of engagement with teeth 44 of worm gear 42 without disengaging from pins 88.

The connection system shown in FIGS. 3A to 3C allows the connector 29 (FIG. 2) and, consequently shaft 18, to rotate about axis C of element 36 and axis B of universal joint 35 freely. Free rotation about axis A is only possible when worm 43 is disengaged from teeth 44 as described above. Otherwise, rotation is controlled by driving either input 76 or 78, thereby rotating worm gear 43 while in engagement with teeth 44.

Referring to FIGS. 4A to 4J, there is shown the coupling system for connecting shaft 18 with first ring 14.

Figure 4A:
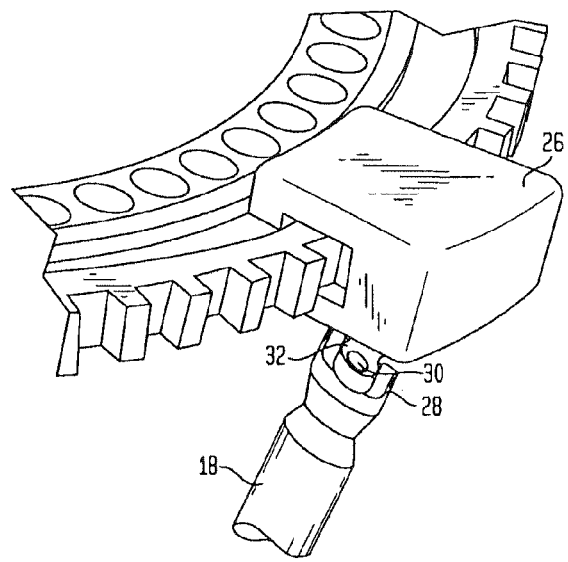
FIG. 4A is an isometric view of a shuttle or sliding unit mounted on the upper ring of the present invention.
Figure 4B:
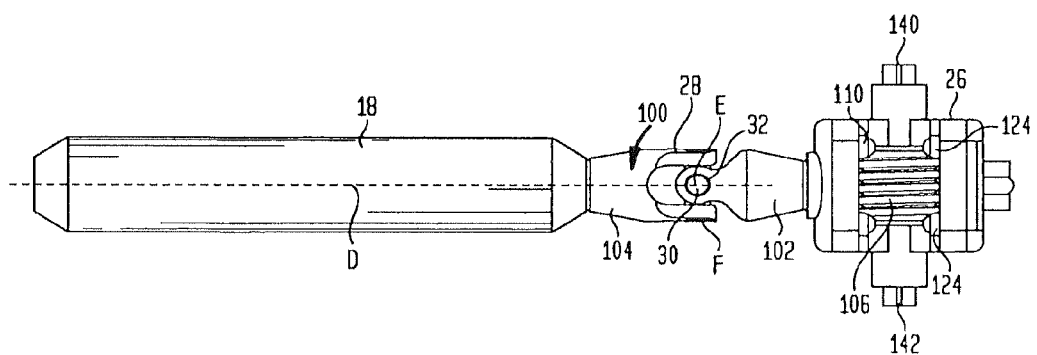
FIG. 4B is an elevation view of the shaft and universal joint and connector of 4A.

Referring to FIG. 4B, there is shown shaft 18 connected by a universal joint 100 which allows rotation about three axes D, E, and F. Connector 26 is coupled to shaft 18 and includes a worm 106, which engages teeth 15 of ring 14. This engagement is seen in FIGS. 4C through 4E in which connector 26 is shown being connected to ring 14 and locked thereon.

Referring to FIGS. 4C to 4J, there is shown ring 14 having a pair of grooves 17, which extend around the circumference of the ring adjacent teeth 15. Connector 26 includes a housing or body 108, which rotatably receives worm 106 and which has a first pair of pins 110 mounted on an arm 112 of housing 108. Each of pins 110 includes a head 114 adapted to be inserted in groove 17 of ring 14. Connector 26 also includes a movable element 116, which may slide toward and away from housing 108 by the action of lever 118, which includes a cam element 120. Lever 118 is rotatable about a pivot pin 122, which is mounted on movable element 116. Movable element 116 also includes a second pair of pins 124 each having a head 126, which, like head 114 of pin 110, can engage groove 17 of ring 14. Pins 124 are fixed on moveable element 116.

As can be seen in the figures, lever 118 can be rotated into a position in which a spring element (not shown) moves movable element 116 away from engagement with body 108 of connector 26 and consequently moves pins 124 upwardly in the figures, which allows connector 26 to be moved laterally into engagement with the ring 14. As shown in FIG. 4D, once the connector 26 is properly positioned with respect to groove 17, lever 118 can then be rotated as shown in FIG. 4E, such that the cam 120, which rotates about pivot pin 122, which is fixed with respect to body 108, forces movable element 116 downwardly such that pins 124 are engaged in the upper groove 17 and pins 110 are engaged in the lower groove 17. The heads 114 and 126 of pins 110 and 124 are sized with respect to groove 17 such that the connector 26 may slide around the circumference of ring 14. Pins 110 and 124 are spaced such that are capable of engaging the grooves 17 of multiple diameter rings. As shown in FIGS. 4G and 4I, worm 106 of connector 26 can be moved into and out of engagement with the teeth 15 of ring 14 while the connector 26 is mounted on groove 17 of ring 14. This can be accomplished as shown in FIGS. 4H and 4J in which elements 130 and 132 can be moved with respect to portions 134 and 136 of the drive shaft for worm 106. Elements 130 and 132, in the preferred embodiment are identical to elements 56 and 58 described with respect to FIGS. 3A and 3C. The other elements of the systems, including springs 62 and 64 are also identical. Thus, FIGS. 4G and 4H show worm 106 in a position which is out of engagement with teeth 15 of ring 14 with FIGS. 4I and 4J showing worm 106 moved into a position where the worm 106 engages the teeth 15 of ring 14.

Figure 4F:
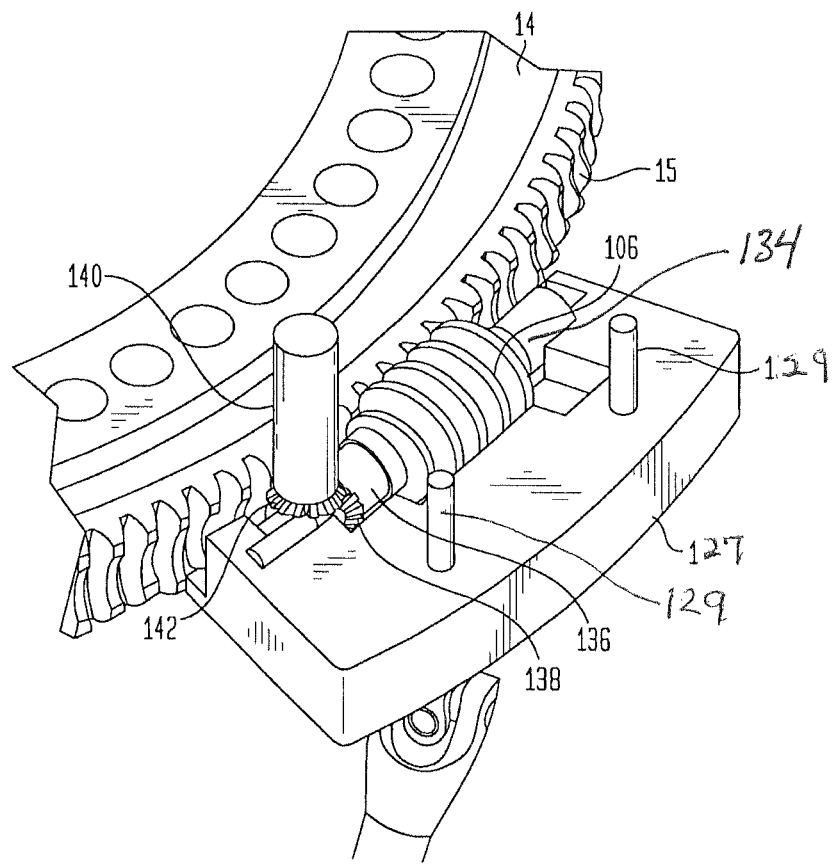
FIG. 4F shows a drive system for the shuttle or sliding unit of the present invention when mounted on the ring of FIG. 4A.

Referring to FIG. 4F, there is shown an alternate drive system for the shuttle or sliding unit 26 of the present invention. As with the connector shown in FIGS. 3A to 3C, unit 26 is driven around the circumference of ring 14 by turning drive elements 140 and 142. This may be done either with a hand tool or a power tool. As can be seen from FIG. 4G, the drive is preferably either a male or female square drive element. The alternate system shown in FIG. 4F includes worm gear 106 mounted in a lower base portion 127 and connected to an upper portion (not shown) by pins 129 a bevel gear 138 fixably mounted on either shaft portion 134 or 136 of worm 106. A drive shaft 140 extending generally perpendicular to the axis of shaft portions 134 and 136, which shaft 140 includes a drive gear 142 may also be used to drive worm 106.

Referring to FIG. 4A, there is shown an enlarged view of an alternate ring 14, including a shuttle or sliding unit 26 mounted on ring 14. Shuttle unit 26 is coupled to a first end 28 of each strut 18. Shuttle unit 26 includes a drive system for moving the shuttle about the circumference of ring 14. The drive system includes a server or stepper motor which is controlled by software on a computer, which determines adjustments to the location of shuttle 26 about the circumference of ring 14 during use of the external fixation system. These adjustments are performed on a daily basis. The computer system software incorporates the input from potentiometers and/or optical encoders and/or other position sensors at the various joints in the external fixation system to determine both the initial position of the system as well as to confirm that the daily adjustments are being made properly.

The ends 28 of strut 18 are connected to shuttle 26 via a standard universal joint-type connector. As shown in FIGS. 4A, 4B, a pivot pin 30 mounted within a pair of bushings 32 on axis or rotation of the universal joint with an additional axis of rotation coaxial with the longitudinal axis of each strutting team and a third axis similar to axis 30 thus forming a typical universal joint.

In some embodiments, sliding unit 26 in the gear portion 42 are driven by a worm gear, which in turn is driven by a stepper or servo motor having an output shaft with a bevel gear, which may be a miter gear. As such there are three independent struts having movable first and second ends 28 and 34 connected to the first and second rings, respectively. Each of the three struts 18 may be moved around the circumference of the first ring 14 by the stepper/slash servo motors driving sliding unit 26. In addition, the second end 34 of rod 18, although circumferentially fixed in a single hole 24 of ring 16, can be rotated in planes perpendicular to the plane of ring 16 by its dedicated stepper or servo motor. The combination of these movements is capable of orienting ring 16 and ring 14 in an infinite number of angular positions with respect to one another. This change in orientation can be accomplished with fixed length struts 18.

The external fixation system of the present invention is normally supplied as a kit with a plurality of rings of different diameters, some of which are either fully circular rings or partial rings allowing their placement over the limb to be treated in a medial-lateral direction. In addition, struts 18 of various fixed lengths can be provided in the kit to produce various axial distances between the centers of the first and second rings 14, 16, respectively. Each strut 18 supplied has first and second ends 28, 34 capable of being connected to the sliding unit 26 and second ring connector 29 as described above.

Figure 6:
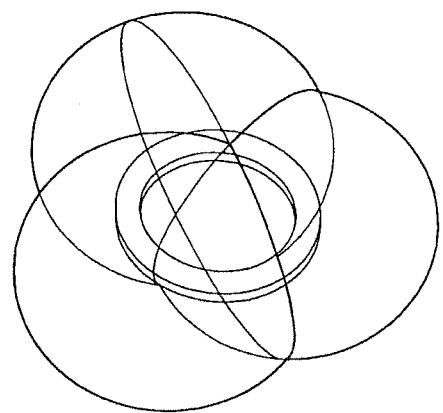
FIG. 6 is a plurality of spherical surfaces showing the movement of the end of one of the three struts shown in FIG. 1.
Figure 7:
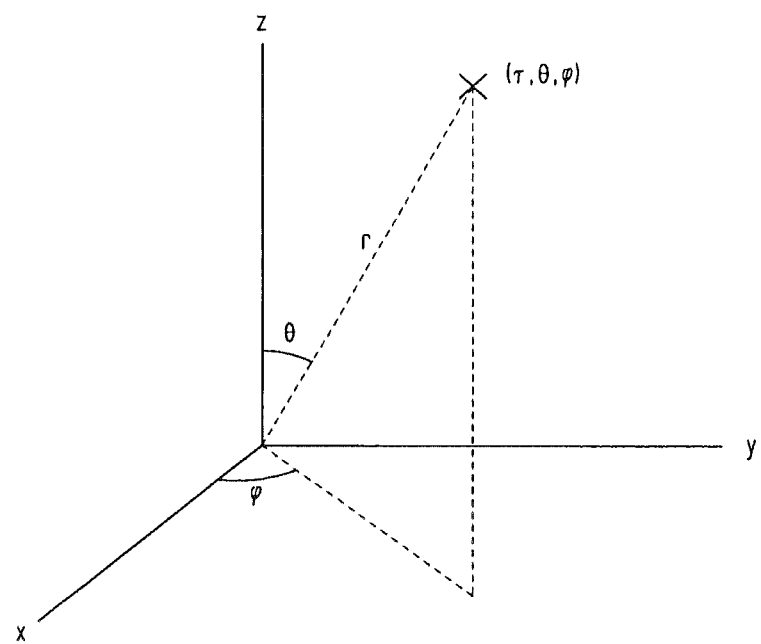
FIG. 7 is a geometric representation of the strut and attached to the first upper ring at its upper end to the second lower ring at its origin.

A controller will also be provided, including microprocessors programmed to implement the various inputs to these six steppers or servo motors of the system. With reference to FIGS. 5-7, the following is a mathematical description of the upper (moving) ring 14 and the base points on the lower (relatively fixed) reference ring 16. We will describe the upper ring as a circle on a plane. The three points $P_{B1}$, $P_{B2}$ and $P_{B3}$ represent the fixed base points on the lower ring 16. The two rings 14, 16 are connected by three struts 18. Each strut 18 is capable of rotating about its fixed base point ($P_{B1}$, $P_{B2}$ or $P_{B3}$) and connects to the upper ring 14 at their respective end points (P1, P2 and P3). The end points (P1, P2 and P3) can lie anywhere on the perimeter of the upper ring 14. The range of motion of the end point of a strut (P1, P2 or P3) can be thought of as the surface of a sphere whose center is the strut's base point and whose radius (r) is the length of the strut. This is visually represented in FIG. 6. The base points are fixed and described in FIG. 5. The length between the base points (PB1, PB2 and PB3) is d. The upper ring 14 has a radius R1.

Any Point in Space $P(X,Y,Z)$ $X = r \sin(\theta)\cos(\phi)$ $Y = r \sin(\theta)\sin(\phi)$ $Z = r \cos(\theta)$ The Points at the End of the Struts These make up the three coplanar points that will connect the struts to the upper ring. They will always be coplanar as they are all connected to a common ring.

Point 1 ($P_1$):

$X_1 = r \sin(\theta)\cos(\phi)$ $Y_1 = r \sin(\theta)\sin(\phi)$ $Z_1 = r \cos(\theta)$ Point 2 ($P_2$):

$X_2 = r \sin(\theta)\cos(\phi) + d \sin(15)$ $Y_2 = r \sin(\theta)\sin(\phi) + d \cos(15)$ $Z_2 = r \cos(\theta)$ Point 3 ($P_3$):

$X_3 = r \sin(\theta)\cos(\phi) + d \cos(15)$ $Y_3 = r \sin(\theta)\sin(\phi) + d \sin(15)$ $Z_3 = r \cos(\theta)$ The Vectors from P1 to P2 and P1 to P3

Using the three points at the end of the struts, we can find two vectors on the plane.

$P1P2 = \hat{a} = <(X2-X1),(Y2-Y1),(Z2-Z1)>$ $P1P3 = \hat{b} = <(X3-X1),(Y3-Y1),(Z3-Z1)>$ The Normal Vector of Plane 2 that the Points P1, P2 and P3 Sit on Using the two vectors on the plane, we can find the normal vector.

$$n = \hat{a} \times \hat{b} = ((Y2-Y1)(Z3-Z1))i + ((Z2-Z1))((X3-X1))j +$$
$$((X2-X1)(Y3-Y1))k - ((Z2-Z1)(Y3-Y1))i -$$
$$((X2-X1)(Z3-Z1))j - ((Y2-Y1)(X3-X1))k =$$
$$((Y2-Y1)(Z3-Z1) - (Z2-Z1)(Y3-Y1))i +$$
$$((Z2-Z1)(X3-X1) - (X2-X1)(Z3-Z1))j +$$
$$((X2-X1)(Y3-Y1) - (Y2-Y1)(X3-X1))k$$

For simplicity's sake, we'll set vector "n" to: n=<a, b, c>

The Equation of "Plane 2" that P1, P2 and P3 sit on

The following describes the upper ring's plane at any given time.

General equation of a Plane: $AX+BY+CZ+D=0$

To solve for the equation of the plane we must find A, B, C and D by setting the determinant of the matrix below equal to zero $$\det \begin{vmatrix} x-x1 & y-y1 & z-z1 \\ x2-x1 & y2-y1 & z2-z1 \\ x3-x1 & y3-y1 & z3-z1 \end{vmatrix} =$$

$$X[y3(z1-z2) + y1(z2-z3) + y2(-z1+z3)] +$$
$$Y[x3(-z1+z2) + x2(z1-z3) + x1(-z2+z3)] +$$
$$Z[-x2*y1 + x3*y1 + x1*y2 - x3*y2 - x1*y3 + x2*y3] +$$
$$[x3*y2*z1 + x2*y3*z1 - x3*y1*z2 +$$
$$x1*y3*z2 + x2*y1*z3 - x1*y2*z3] = 0$$

Where the coefficient of X is A, the coefficient of Y is B, coefficient of Z is C and the rest is the constant D.

Equation of Sphere

To solve for the upper ring we must find the equation of a sphere. This sphere will share the upper ring's center point and radius "R1". The sphere will also have P1, P2 and P3 on its surface. The plane we solved for above passes through the sphere's center and contains P1, P2 and P3. Therefore, the intersection of this sphere and the plane will describe the equation of the circle we are ultimately solving for to represent the upper ring.

Since P1, P2 and P3 are on the sphere's surface, the distance from these points to the center of the sphere will be equal. Setting up the following three equations will allow us to solve for the center point (Xc, Yc, Zc).

Given R1, P1, P2, P3 and the General Equation of a Sphere:

$(X-X_{center})^2 + (Y-Y_{center})^2 + (Z-Z_{center})^2 = R1^2$

We can solve for (Xc, Yc, Zc):

$(X1-Xc)^2 + (Y1-Yc)^2 + (Z1-Zc)^2 = R1^2$

And $(Xc-X1)^2 + (Yc-Y1)^2 + (Zc-Z1)^2 = (Xc-X2)^2 + (Yc-Y2)^2 + (Zc-Z2)^2$

And $(Xc-X1)^2 + (Yc-Y1)^2 + (Zc-Z1)^2 = (Xc-X3)^2 + (Yc-Y3)^2 + (Zc-Z3)^2$

Solve for (Xc, Yc, Zc)

The Cartesian Equation of the Circle

Given the center (Xc, Yc, Zc) (from the sphere above), the normal vector n=<a, b, c> (from the plane) and the three points P1, P2 and P3 (on the circle); the Cartesian representation of the circle is:

$(X-Xc)^2 + (Y-Yc)^2 + (Z-Zc)^2 = R1^2$

And $$X[y3(z1-z2) + y1(z2-z3) + y2(-z1+z3)] +$$
$$Y[x3(-z1+z2) + x2(z1-z3) + x1(-z2+z3)] +$$
$$Z[-x2*y1 + x3*y1 + x1*y2 - x3*y2 - x1*y3 + x2*y3] +$$
$$[x3*y2*z1 + x2*y3*z1 - x3*y1*z2 +$$
$$x1*y3*z2 + x2*y1*z3 - x1*y2*z3] = 0$$

Parametric Equation of Circle

With the center being (Xc, Yc, Zc) (from the sphere above) and the normal vector being n=<a, b, c> (from the plane), the Parametric representation of the ring is:

$$X(t)=Xc+(a{*}c{*}R{*}\cos(t)-b{*}R{*}\sin(t)/(a\char`\^2+b\char`\^2)\char`\^(\tfrac{1}{2})$$

$$Y(t)=Yc+(b{*}c{*}R{*}\cos(t)+a{*}R{*}\sin(t)/(a\char`\^2+b\char`\^2)\char`\^(\tfrac{1}{2})$$

$$Z(t)=Zc-R{*}\cos(t){*}(a\char`\^2+b\char`\^2)\char`\^(\tfrac{1}{2})$$

Where: $0 \le t \le 2\pi$

EXAMPLE

Thus, to align a first bone element with respect to a second bone element, one utilizes the above mathematical model to design software. The software will first consider the initial position of the rings with respect to the bone elements. The final position of the frame with the aligned bones will be determined by the software, taking into account the size and position of the rings and struts. The software will calculate the shortest trajectory from the initial to final position of the moving ring, generating the intermediate positions of the moving elements on the ring, and the angular rotations of the struts at the fixed ends, using a form of ring kinematics to get the necessary values. The ring kinematics will be derived by applying the mathematical formula above to determine the iterations required to get from the initial position to the final position. These iterations will be generated with a constraint on the maximum possible correction per day as defined by the surgeon in terms of the maximum distraction rate.

Figure 8:
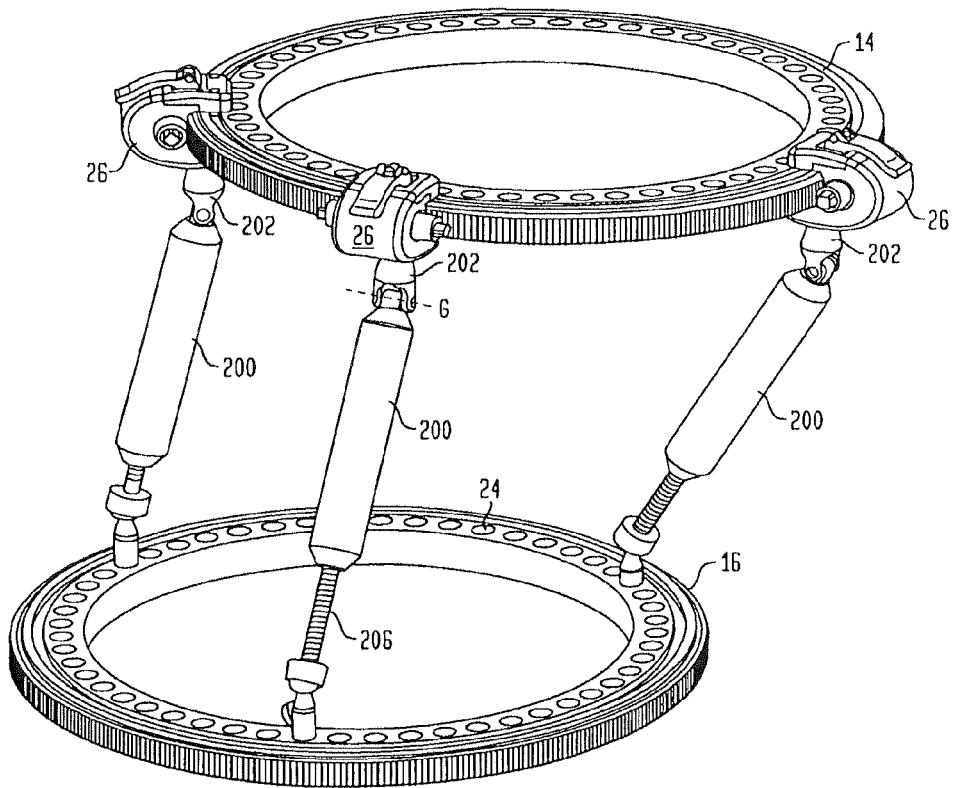
FIG. 8 is an isometric view of an alternate embodiment of the external fixation system of the present invention.
Figure 11:
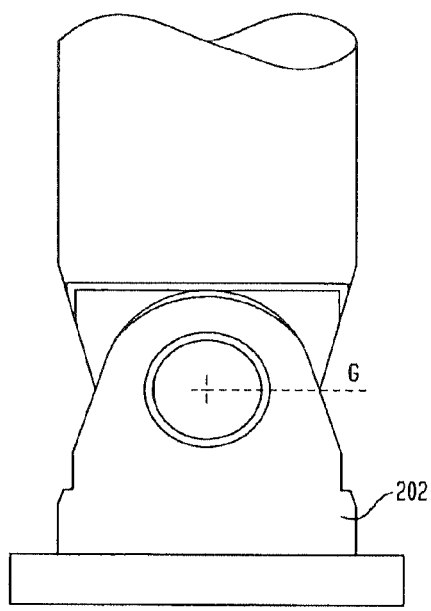
FIG. 11 is an elevation view of the strut.
Figure 12:
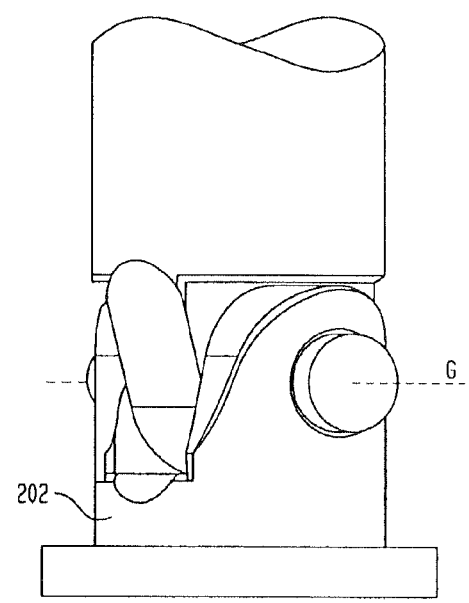
FIG. 12 is an isometric view of the strut end of FIG. 11.

Referring to FIGS. 8-13, there is shown an alternate embodiment of the present invention. Referring to FIG. 8, there is shown a manipulator having a pair of rings identical to the rings 14 and 16 of the preferred embodiment. Ring 14 includes three sliding units 26 which are identical to those shown in FIGS. 4B-4J. Three identical struts 200 are utilized in the alternate embodiment which struts have an adjustable length. In this embodiment, the struts are connected to the sliding units 26 via a yoke 202, which is shown in FIGS. 11 and 12 and which allows rotation about a single axis G. The other end of each strut 200 is connected to the ring 16 via an expandable coupling element 204, which is inserted in one of the holes 24 in ring 16. As will be discussed below, yoke 202 is attached to sliding unit by a ball and socket joint. As shown in FIGS. 9 and 10, expandable coupling 204 is connected to one element of the strut 200, which may be a threaded rod 206 to allow adjusting of the length of the strut 200. The connection between the coupling element 204 and the threaded rod 206 is by a ball joint 208 which allows rotation about three axes. Since threaded rod 206 is received within a threaded bore (not shown) in the upper portion of strut 200, rotation of rod 206 about the ball joint 208 along the longitudinal axis of the rod 206 increases or decreases the length of the strut 200.

Sliding unit 26 operates as described above in connection with the embodiment depicted in FIG. 2 to move the upper ends of the struts 18 around the circumference of ring 14. When not being driven, sliding unit 26 is fixed firmly in position on ring 14. Attaching the upper end of yoke 202 to the sliding unit 26 is via a similar ball and socket joint as ball and socket joint 208 which will allow the strut and sliding unit to articulate relative to each other about the three rotational axes of a spherical joint, allowing for three degrees of freedom in the kinematic chain. Alternately, strut 18 could attach to a rotationally fixed, separate piece which would form the socket. As shown in FIG. 10, in order to keep the spherical joint in tact while unloaded, it is desired to include a separate cap 212, which threads onto the end of rod 206 to ensure that the ball does not slip out of the socket.

Figure 13:
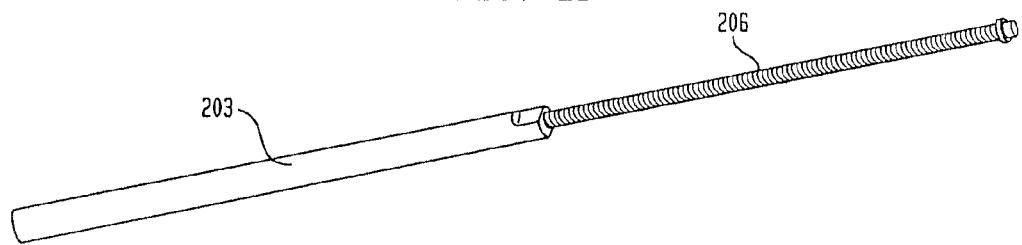
FIG. 13 is an elevation view of the extension mechanism of the strut of the alternate embodiment of FIG. 8.

As shown in FIG. 13 strut 200 is, as discussed above, formed out of two pieces, one being threaded rod 206 and the upper section including a part 203 with a threaded bore receiving rod 206.

Figure 14:
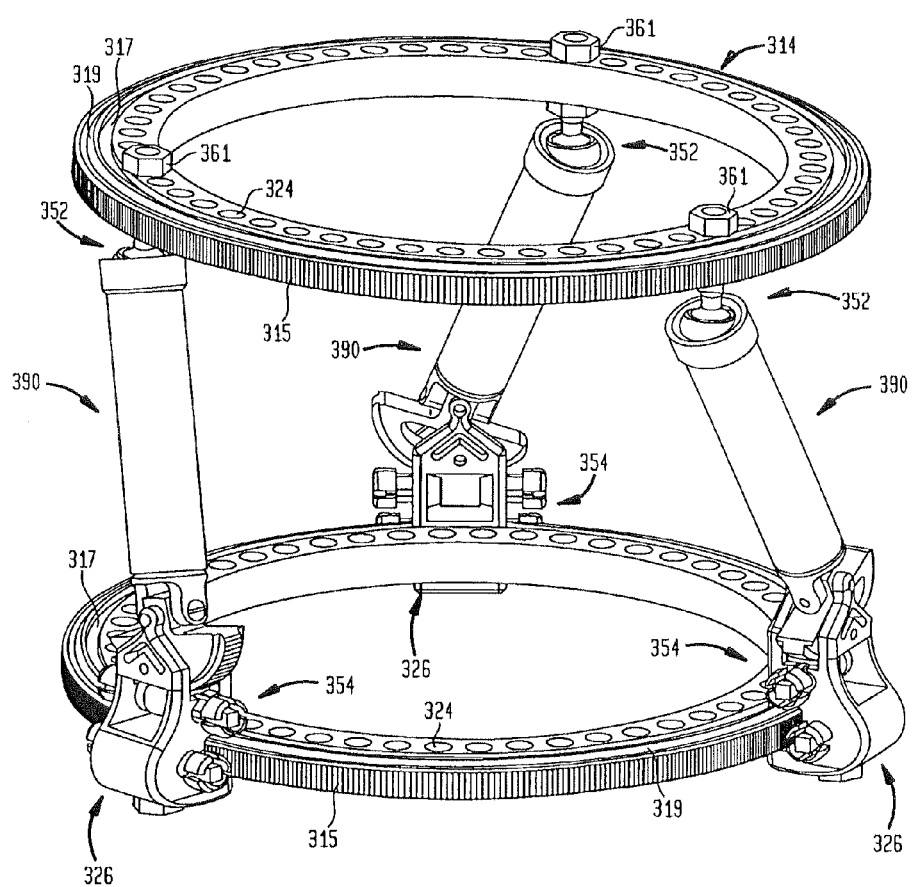
FIG. 14 is an isometric view of an alternate embodiment of the external fixation system of the present invention.

Referring to FIG. 14, an alternate embodiment of the presently disclosed external fixation system is generally designated as 300. External fixation system 300 includes a first platform or ring 314, a second platform or ring 316, and a plurality of non-prismatic kinematic chains or struts 390 each connecting the first platform 314 to the second platform 316. For the purposes of the present disclosure, the term "prismatic" means an element or joint with one translational degree of freedom. Usually, prismatic kinematic chains or struts are extendable and can therefore vary their lengths along their longitudinal axis during actuation. On the contrary, the term "non-prismatic" refers to a joint or element incapable of changing its length along its longitudinal axis upon actuation. Thus, the term "non-prismatic kinematic chain," as used herein, means a kinematic chain that does not varies its length along its longitudinal axis during actuation.

In the embodiment depicted in FIG. 14, external fixation system 300 includes three non-prismatic kinematic chains 390 but external fixation system 300 may have more non-prismatic kinematic chains 390. For example, certain embodiments of external fixation system 300 may have four or even six non-prismatic kinematic chains 390. Regardless of the specific number of non-prismatic kinematic chains 390, each kinematic chain 390 connects the first platform 314 to the second platform 316 and has a first end portion 352 and a second end portion 354. First end portions 352 of each kinematic chain 390 are connected to first platform 314, whereas second end portions 354 of each kinematic chain 390 are connected to second platform 316. As a consequence, kinematic chains 390 maintain first and second platforms 314, 316 spaced apart from each other. However, the distance and orientation between first and second platforms 314, 316 may vary as one or more kinematic chains 390 move relative to one another.

First and second platforms 316, 314 are substantially similar to first and second rings 14, 16, as described above, and to each other. Nevertheless, first and second platforms 314, 316 may be made of different materials. For example, in certain embodiments, first platform 314 is wholly or partly made of aluminum, while second platform 316 is wholly or partly made of a radiolucent carbon fiber or a reinforced polymer such as polyetheretherketone (PEEK).

Figure 15:
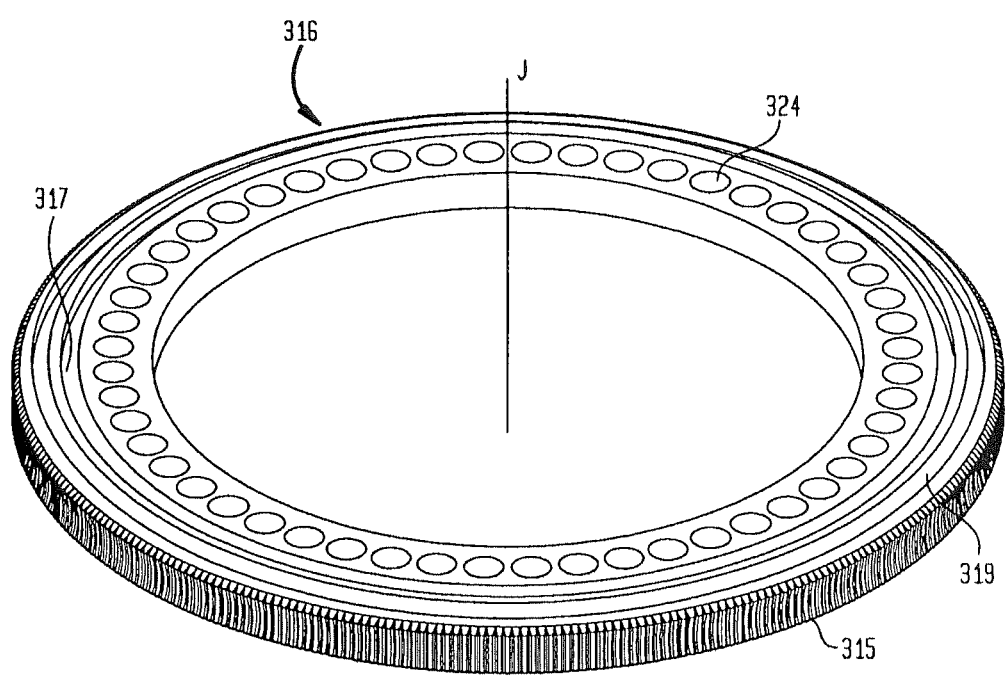
FIG. 15 is an isometric view of a ring or platform of the external fixation system shown in FIG. 14.

As seen in FIG. 15, second platform 316 has a chamfer 319 extending along its circumference in addition to holes 324, groove 317, and worm gear 315. As with second ring 16, second platform 316 has grooves 317 on opposite sides. Grooves 317 extend along the circumference or perimeter of second platform 316. Chamber 319 is located radially outwardly with respect to groove 317 and facilitates connection of kinematic chains 390 to second platform 316 as discussed in detail below. In some embodiments, second platform 316 has a planar configuration and defines a plane. In these embodiments, an axis J extends orthogonally relative to the plane defined by second platform 316. First platform 314 is substantially similar to second platform 316 and also includes a chamfer 319 extending along its circumference (see FIG. 14).

Figure 16:
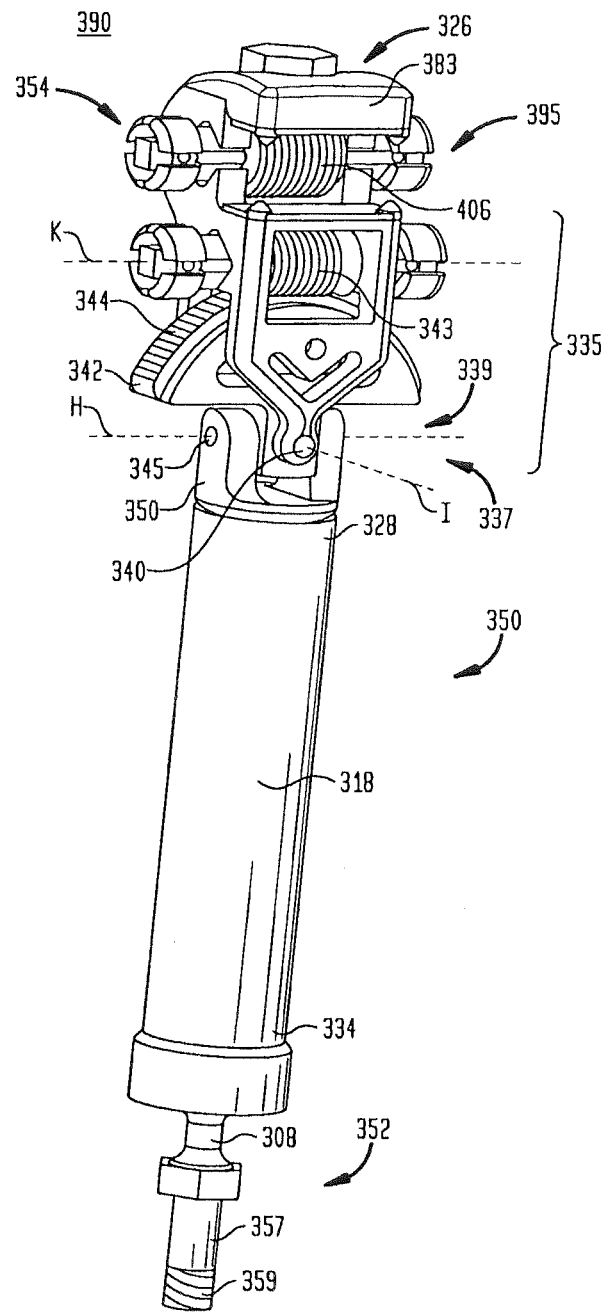
FIGS. 16 and 17 are isometric views of a kinematic chain of the external fixation system shown in FIG. 14.
Figure 17:
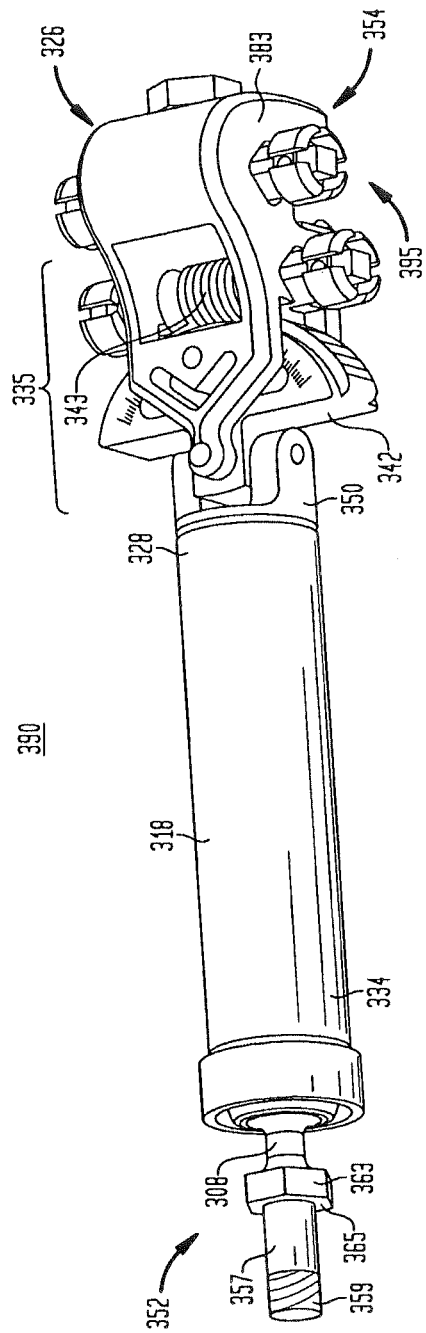
Figure 18:
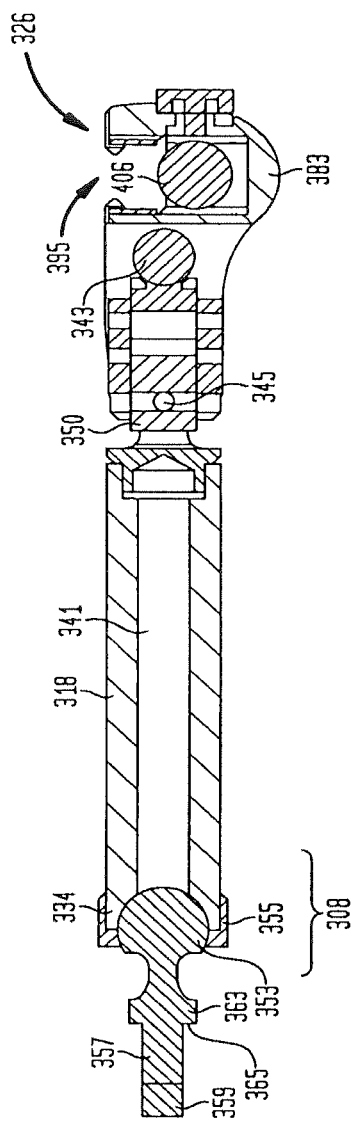
FIG. 18 is cross-sectional view of the kinematic chain shown in FIGS. 16 and 17.
Figure 19:
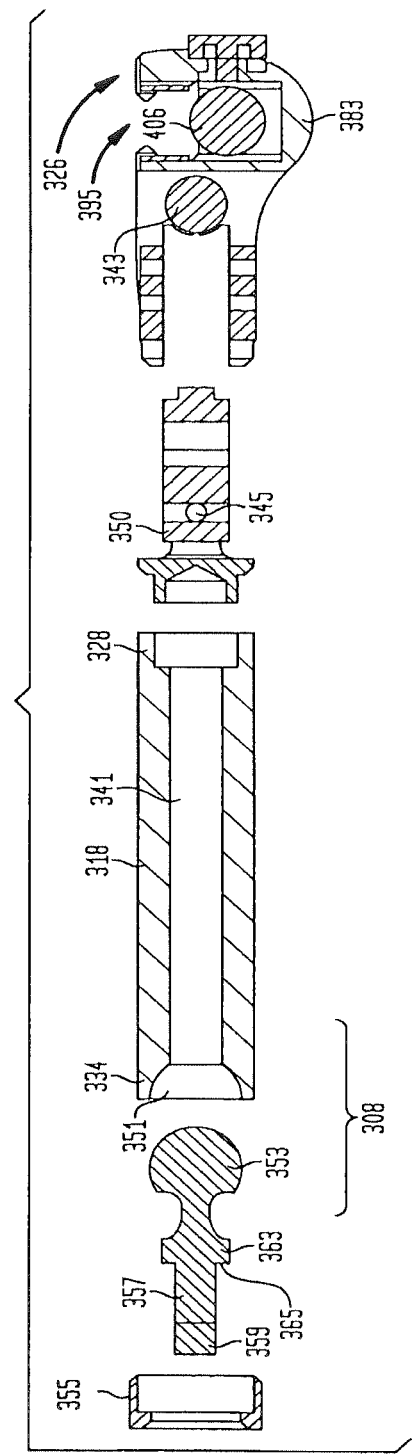
FIG. 19 is an exploded cross-sectional view of the kinematic chain depicted in FIGS. 16 and 17.

With reference to FIGS. 16-17, each kinematic chain 390 includes a shaft 318 positioned between first and second end portions 352, 354, a spherical joint 308 located at first end portion 352, a universal joint 335, and a sliding unit 326 positioned at second end portion 354. Shaft 318 has a first end 328 and a second end 334 and connects universal joint 335 to spherical joint 308. In particular, universal joint 335 is connected to first end 328 of shaft 318, while spherical joint 308 is coupled to second end 334 of shaft 318. As shown in FIGS. 18 and 19, shaft 318 is hollow and has a bore 341 extending between first and second ends 328, 334. Shaft 318 may be wholly or partially made of a radiolucent material. In certain embodiments, shaft 318 is made of a titanium alloy (Ti6Al4V). Second end 334 of shaft 318 includes a socket 351, which is part of spherical joint 308.

With reference to FIGS. 18-19, spherical joint 308 includes a socket 351 formed within second end 334 of shaft 318 and a ball 353 dimensioned to be received in socket 351. In operation, spherical joint 308 provides three degrees of rotational freedom and facilitates movement of kinematic chain 390 with respect to first platform 314. A cap 355 is positioned around second end 334 of shaft 318 and engages ball 353, thereby maintaining a portion of ball 353 within socket 351 without inhibiting the movement of ball 351. A connecting member 357 extends from ball 351 and is dimensioned to be received within a hole 324 of either first platform 314 or second platform 316. Connecting member 357 includes a threaded end portion 359 (FIG. 16) adapted to mate with a nut 361 (see FIG. 14) and a base end portion 363 having a flat surface 365. When spherical joint 308 is connected to first platform 314, flat surface 365 of base end portion 363 engages one side of first platform 314, while nut 361 engages another side of first platform 314. To connect spherical joint 308 to first platform 314, connecting member 357 is inserted through one of the holes 324 of first platform 314 until flat surface 365 of base end portion 363 engages one side of first platform 314. Then, nut 361 is threaded onto threaded end portion 359. After threading nut 361 onto threaded end portion 359 of connecting member 357, nut 361 fastens spherical joint 308 to first platform 314, as seen in FIG. 14.

Referring again to FIGS. 16-19, sliding unit 326 includes a first revolute joint 395 and universal joint 335, which itself includes second and third revolute joints 337, 339. Universal joint 335 is substantially similar to universal joint (FIG. 3A). Second and third revolute joints 337, 339 provide universal joint 335 with two degrees of rotational freedom. Second revolute joint 337 is configured to rotate about axis H, while third revolute joint 339 is adapted to rotate about axis I. Axis H is oriented substantially orthogonal to axis I. A yoke or housing 350 connects universal joint 335 to first end 328 of shaft 318 and holds a pivot pin 345 axially aligned along axis H.

Figure 20:
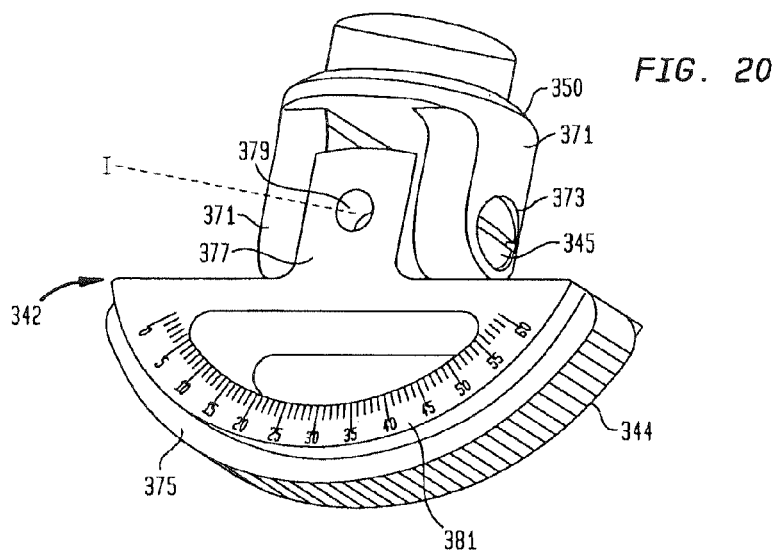
FIG. 20 is an isometric view of a gear portion, a yoke, and a pin of the kinematic chain shown in FIGS. 16 and 17.
Figure 21:
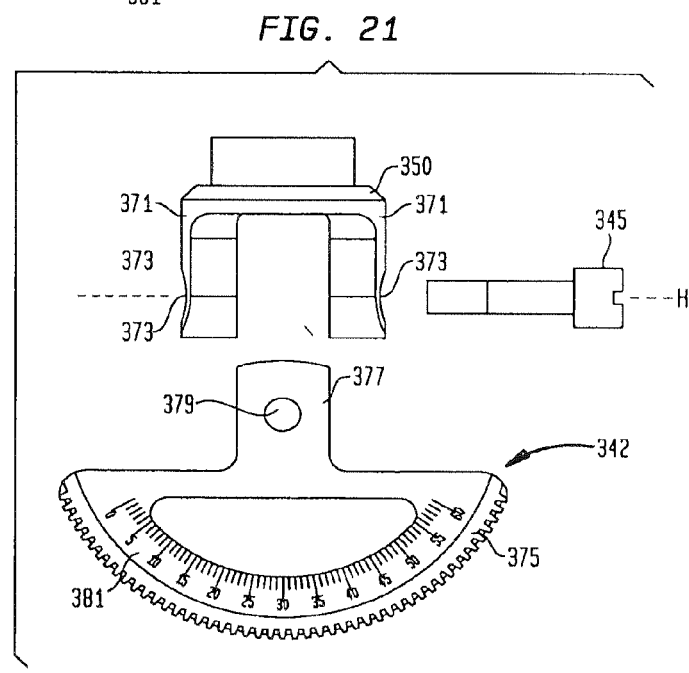
FIG. 21 is an exploded view of the gear portion, the yoke, and the pin depicted in FIG. 20.

Referring to FIGS. 20 and 21, yoke 350 includes two legs 371 oriented substantially parallel to each other. Each leg 371 includes a bore 373 longitudinally aligned with axis H and dimensioned to receive pivot pin 345. Pivot pin 345 extends through bores 373 of yoke 350 and pivotally couples a gear portion or worm gear 342 of universal joint 335 to yoke 350. Gear portion 342 is substantially similar to gear portion 42 (FIG. 3A) and includes a driving section 375 and a connecting section 377 extending from driving section 375. Connecting section 377 is sized to be received between legs 371 of yoke 350 and has a bore (not shown) substantially aligned with axis H and dimensioned to receive pivot pin 345. When assembled, pivot pin 345 extends through bores 373 of yoke 350 and the bore of driving section 375 aligned with axis H, thereby pivotally coupling gear portion 342 to yoke 350. As a result of this mechanical arrangement, second revolute joint 337 can rotate about pivot pin 345, which is positioned substantially parallel to axis H.

With continued reference to FIGS. 20 and 21, gear portion 342 of universal joint 335 aids in the rotation of third revolute joint 339. To this effect, connecting section 377 of gear portion 342 has a bore 379 axially aligned with axis I (see FIG. 16). As discussed in detail below, bore 379 is dimensioned to receive pivot pin 340. Aside from bore 379, gear portion 342 includes gear teeth 344 formed along a perimeter of driving section 375. In the depicted embodiment, driving section 375 has a semi-circular shape but driving section 375 may have any other suitable shape or configuration. Driving section 375 of gear portion 342 further includes markings indicating the angulation of shaft 318 with respect to sliding unit 326 (FIG. 14).

Referring again to FIGS. 16-19, gear teeth 344 of gear portion 342 are configured to engage the teeth of drive connector or worm 343. Drive connector 343 is substantially similar to worm 43. Worm 343 and gear portion 342 collectively form a worm gear drive system and are part of third revolute joint 339. As discussed above, third revolute joint 339 can rotate pivot pin 340, which is axially aligned with axis I. Pivot pin 340 is dimensioned to be received in bore 379 (FIG. 21) of gear portion 342 and pivotally connects gear portion 342 to a clamp body 383 of sliding unit 326.

Clamp body 383 of sliding unit 326 holds parts of third revolute joint 339, i.e., gear portion 342 and worm 343. Worm 343 is configured to engage gear portion 342. As a result, gear portion 342 pivots about axis I upon rotation of worm 343 about axis K when gear portion 342 and worm 343 are engaged to each other. As discussed with regard to drive connector 43, drive connector 343 can be driven by any suitable mechanical or electro-mechanical tool or means. For example, worm 343 may be driven by a "smart tool" as described in U.S. Pat. No. 6,017,354, a dedicated stepper/servo motor or a hand tool. Since third revolute joint 339 can be pivoted about pivot pin 340 through the actuation of worm 343, third revolute joint 339 is deemed an actuated joint. For the purposes of the present disclosure, an "actuated joint" means any joint capable of being driven or actuated by a mechanical or electro-mechanical tool. In the embodiment illustrated in FIG. 16, the rotation of worm 343 about axis K causes the pivotal movement of third revolute joint 339 about pivot pin 340. Pivot pin 340 pivotally couples gear portion 343 to clamp body 383.

Figure 22:
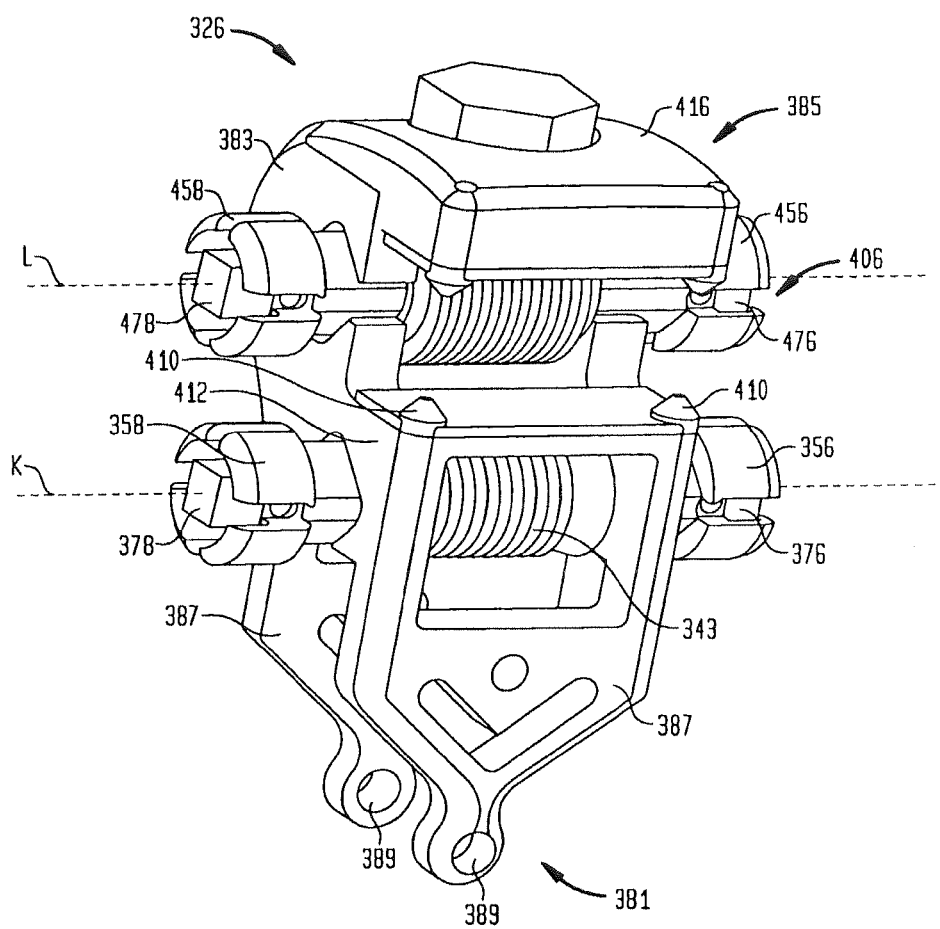
FIG. 22 is an isometric view of a sliding unit of the external fixation system shown in FIG. 14.
Figure 23:
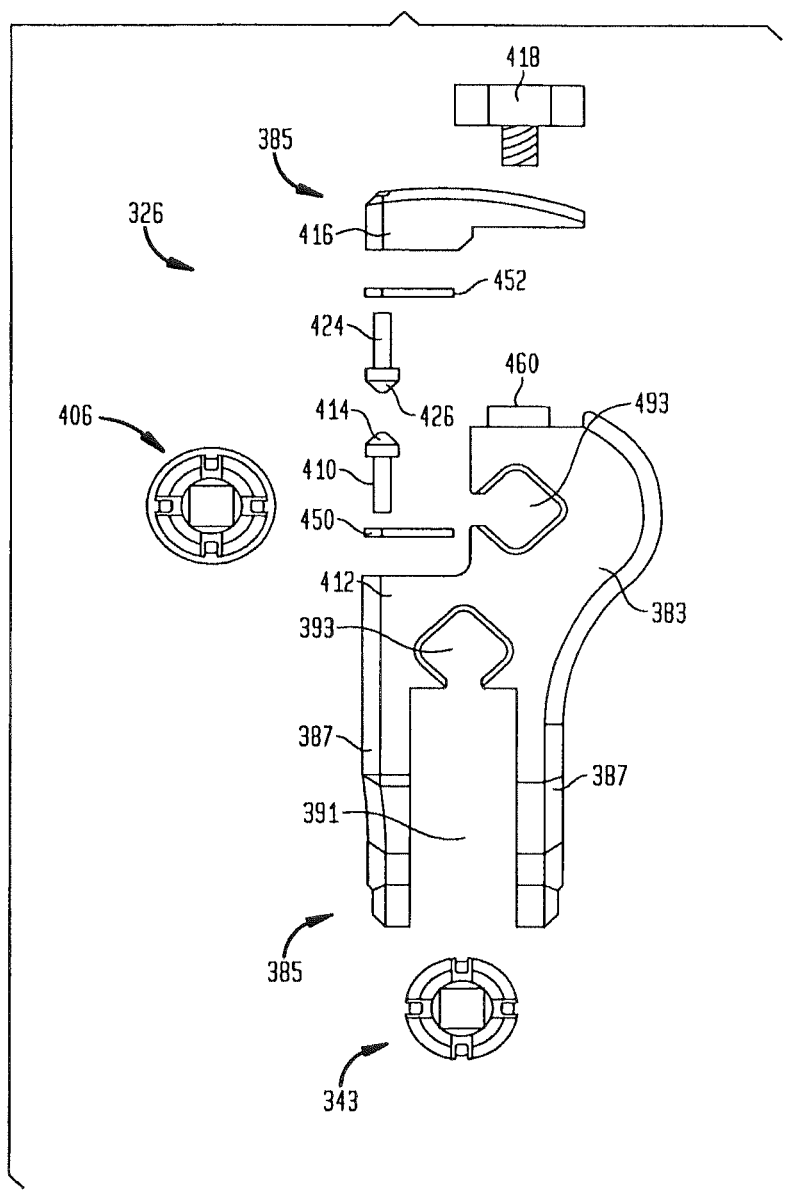
FIG. 23 is an exploded view of the sliding unit shown in FIG. 22.

With reference to FIGS. 22 and 23, clamp body 383 of sliding unit 326 has a first end 381 and a second end 385 and includes a pair of legs 387 extending toward first end 381. Legs 387 are oriented substantially parallel to each other and define a space 391 between them dimensioned to receive gear portion 342 (FIG. 16). Each leg 387 includes a bore 389 dimensioned to receive pivot pin 340. Bores 389 are both axially aligned with axis I (FIG. 16). Pivot pin 340 (FIG. 16) extends through bores 389 of clamp body 383 and bore 379 of gear portion 342 (FIG. 21), connecting clamp body 383 to gear portion 342. Space 391 leads to an opening 393 dimensioned for receiving worm 343. Worm 343 is retractably mounted within opening 393. Accordingly, worm 343 is configured to move between an engaged position relative to gear portion 342 and a disengaged position with respect to gear portion 342. In the engaged position, worm 343 mates with gear portion 342 and, consequently, worm 343 can drive gear portion 342 when rotated about axis K. In the disengaged position, worm 343 does not mate with gear portion 342 and, therefore, cannot drive gear portion 342.

The structure and operation enabling movement of worm 343 between the engaged and disengaged positions are identical to the structure and operation of worm 43 (see FIGS. 3B and 3C). For example, worm 343 is mounted on shafts (not shown), which are in turn received within spring-loaded mounting elements 356 and 358. Mounting elements 356 and 358 are identical to mounting elements and 58. Moreover, mounting elements 356 and 358 are biased inwardly by springs (not shown), which forces worm 343 into engagement with teeth 344 of gear portion 342. When a user moves mounting elements 356 and 358 actually outwardly along the shafts against the force of the springs, the worm 343 can move toward gear portion 342 and into engagement with teeth 344. The springs then lock mounting elements 356, 358 in the engaged position so that shaft 318 may be freely pivoted about axis I (FIG. 16). In addition, worm 343 includes drive elements 376, 378 integrally connected at its ends. Drive elements 376, 378 are identical to drive elements 76, 78. In operation, drive elements 376, 378 facilitate attachment of a driving tool to worm 343. Thus, when a drive tool is attached to either drive element 376 or 378 and rotated, worm 343 rotates about axis K and engages teeth 344, thereby rotating gear portion 342 about axis I (FIG. 16).

Referring again to FIGS. 16-19, each kinetic chain 390 includes a third revolute joint 395 capable of rotating around a perimeter or circumference of second platform 316. Third revolute joint 395 is part of sliding unit 326 and includes a worm 406 that is identical to worm 106 (FIG. 4H).

With reference to FIGS. 22 and 23, worm 406 is retractably mounted in an opening 493 formed adjacent to second end 385 of sliding unit 326. Worm 406 can move between engaged and disengaged positions relative to worm gear 315 of second platform 316 (FIG. 14). In the engaged position, worm 406 mates with worm gear 315 of second platform 316, whereas, in the disengaged position, worm 406 does not mate with worm gear 315 of second platform 315. Worm 406 includes spring-loaded mounting elements 456 and 458 for facilitating engagement and disengagement with worm gear 315 of second platform 316. The structure and operation of mounting elements 456 and 458 are identical to the structure and operation of mounting elements 356 and 358. To move worm 406 between the engaged and disengaged positions, the user should follow procedure discussed above with regard to worm 343. In the case of worm 406, however, the user moves worm 406 toward or away from worm gear 315 after moving mounting elements 458 and 458 outwardly to disengage or engage worm 406 with worm gear 315. In addition, worm 406 includes drive elements 476, 478 integrally connected at its ends. Drive elements 476, 478 are identical to drive elements 376, 378 and facilitate attachment of a driving tool to worm 406.

When worm 406 is located in the engaged position relative to worm gear 406, worm 406 can revolve along the perimeter or circumference of second platform 316 upon rotation of worm 406 about axis L. Worm 406 can be driven (that is, rotated about axis L) with any of suitable mechanical or eletro-mechanical tool or means such as a "smart tool" a dedicated stepper/servo motor or a hand tool. Given that first revolute joint 395 can be actuated through the rotation of worm 406 about axis L, first revolute 395 is deemed an actuated joint. As discussed above, third revolute joint 339 is also considered an actuated joint. Spherical joints 308 are not considered actuated joints because these joints are not driven or actuated. Therefore, each kinematic chain 390 of the embodiment shown in FIG. 14 includes at least two actuated joints. Each kinematic chain 390, however, may include more actuated joints.

With continued reference to FIGS. 22 and 23, sliding unit 326 includes a base 412, a movable arm 416 adapted to move toward and away from base 412, a first pair of pins 410 mounted on base 412, and a second pair of pins 424 mounted on movable arm 416. An open area or space is defined between movable arm 416 and base 416 and is dimensioned to receive either first or second platform 314, 316. This space allows a user to snap sliding unit 326 onto either first platform 314 or second platform 316. First and second pair of pins 410, 424 also help in the connection between sliding unit 426 and either first platform 314 or second platform 316.

The structure and operation of pins 410 are identical to the structure and operation of pins 110 (see FIGS. 4C-4E), and the structure and operation of pins 424 are identical to the structure and operation of pins 124 (see FIGS. 4C-CE). Briefly, each pin 410 has a head 414 adapted to engage groove 317 of either first platform 314 or second platform 316. Likewise, each pin 424 has a head 426 configured to engage groove 317 of either first platform 314 or second platform 316. In operation, heads 414 of pins 410 slide along one groove 317, while heads 424 of pins 424 slide along another groove 317 of the same platform (314 or 316) as sliding unit 326 revolves around the circumference of said platform (314 or 316).

Sliding unit 326 additionally includes a first sheet 450 mounted on base 412 for maintain the position of the first pair of pins 410 and a second sheet 452 mounted on movable arm 416 for maintain the position of the second pair of pins 424.

As discussed above, movable arm 416 can move toward and away from base 412. In some embodiments, a bolt 418 or any other suitable apparatus controls the movement of movable arm 416 relative to base 412 and helps secure sliding unit 426 to second platform 416. Clamp body 383 includes a threaded hole 460 positioned and dimensioned to receive and engage bolt 418. Bolt 418 can secure movable arm 416 to clamp body 383 when securely received within threaded hole 460. A user can move movable arm 416 toward or away from base 412 by screwing or unscrewing bolt 418 from threaded hole 460.

Figure 24:
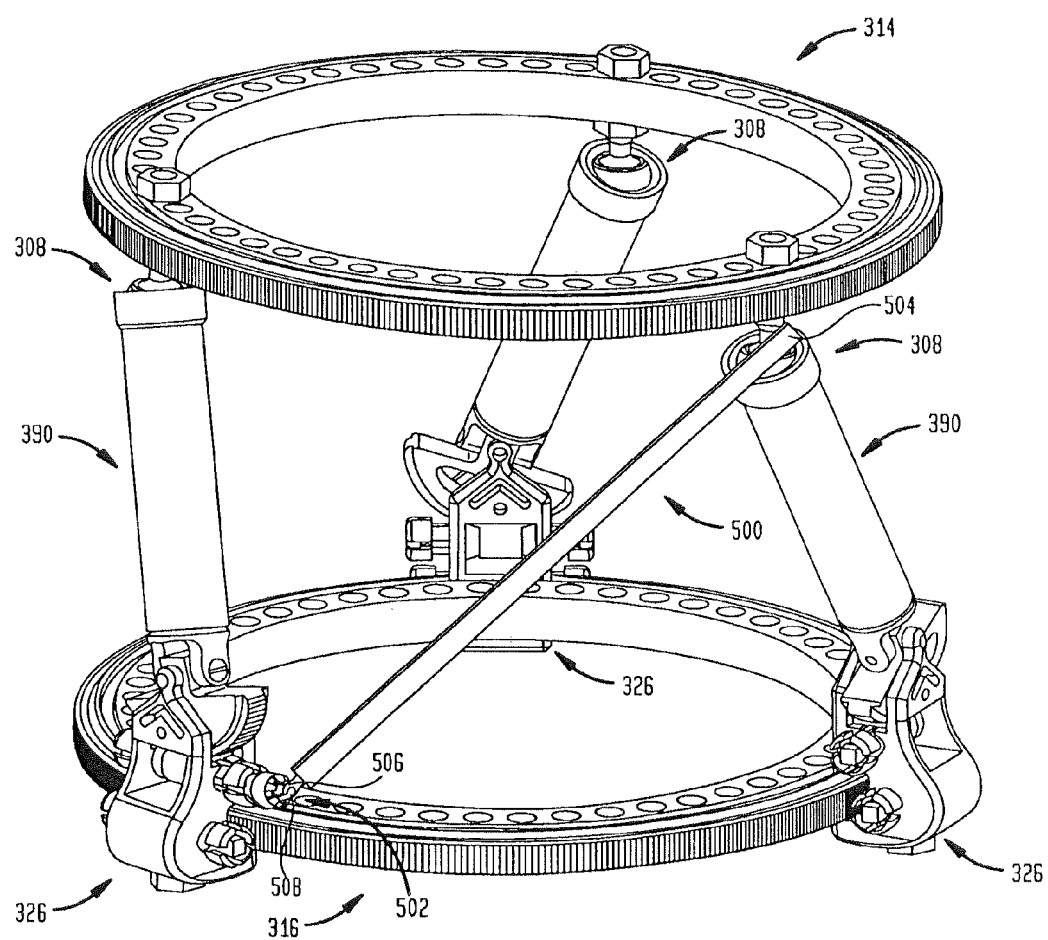
FIG. 24 is an isometric view of a measuring device attached to the embodiment of the external fixation system shown in FIG. 14.

Referring to FIG. 24, a measuring device is generally designated as 500. Measuring device 500 is effectively a measuring tape having a first end 502 and second end 504. First end 502 includes a magnetic component 506 adapted to be connected to drive elements 476 or 478 of worm 406 through magnetism. Magnetic component 506 includes two or more links 508 or any other suitable articulation mechanism. Links 508 allow magnetic component 506 to articulate relative to second end 504. In operation, a user utilizes measuring device 500 to measure the distance between an end of a worm 406 located in one kinematic chain 390 and a spherical joint 308 located in another kinematic chain 390. In the case of an external fixation system with three kinematic chains 390, the user should measure this distance three times. Each time the user should measure such distance between a different pair of kinematic chains 390. Each measurement in effect represents the length of a "phantom strut" of a hexapod, making calculations for the software much simpler.

Figure 25:
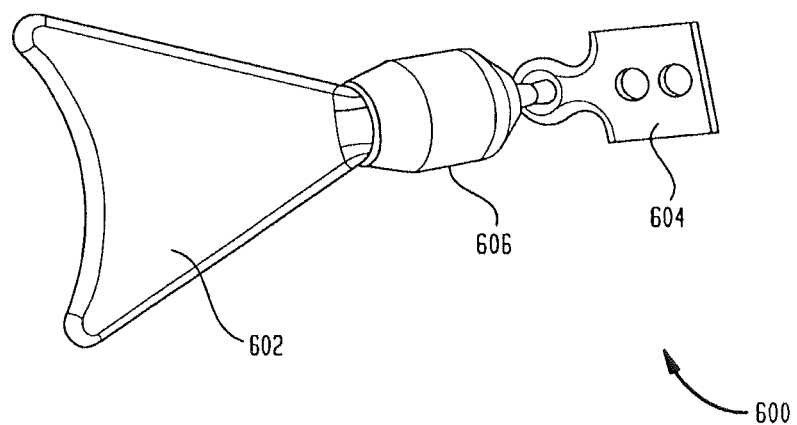
FIG. 25 is an isometric view of a measuring device for determining the distance between the osteotmy site and a ring or platform of the external fixation system.

FIG. 25 shows another measuring apparatus 600 for measuring the distance between the osteotomy site and second platform 316. Osteotomy site refer to the location where the surgeon cuts the bone in two segments before fixing the resulting two bone segments with an external fixation system. Measuring apparatus 600 can be coupled to magnetic component 506 of measuring device 500 through magnetism and includes a planar portion 602 configured to be aligned with the osteotomy site while measuring, a coupling portion 604, and a handle 606 located between planar portion 602 and coupling portion 604. In use, magnetic component 506 of measuring device 500 is initially secured to coupling portion 604 of measuring apparatus 600. Then, the user aligns planar portion 602 with the osteotomy site and subsequently measures the distance between the osteotomy site and second platform 316.

In use, a physician may employ external fixation system 300 as well as the alternate embodiments to perform an osteotomy. Osteotomy may be performed at any long bone such as the tibia and the femur. In an exemplary method, the physician attaches the first platform to a first bone segment with any suitable apparatus such as wires or pins. Then, the physician attaches the second platform to a second bone segment with wires or pins. After securing the first and second platforms to different bone segments, the physician should determine the proper relative position of the first bone segment with respect to the second bone segment (i.e, a predetermined position). Using the software described above, the physician then uses a mathematical correlation of the relative position of the first platform with respect to the second platform to determine the new locations for the actuated joints required to reposition the first bone segment to the predetermined position with respect to the second bone segment. Next, the physician actuates the actuated joints to move said actuated joints to the new determined locations. Other methods of utilizing the disclosed external fixation system are envisioned. Irrespective of the methods employed, the presently disclosed external fixation system provide at least six degrees of freedom.

These components come together to allow the full assembly six degrees of freedom: three translational (x,y,z), and three rotational (pitch, roll, yaw). It is worth noting that the assembly does this with three struts instead of the normal six associated with a Gough/Stewart platform. The mathematics of this system is described in Alizade et al. Mech. Mach. Theory Vol. 29, No. 1, pp. 115-124, 1994 which is incorporated herein by reference in its entirety.

Many authors have proposed six degrees of freedom robots with only three legs that will have two actuators per leg (hence they are not fully parallel). This allows one to decrease the risk of interference between the legs (thereby increasing the workspace size), but has the drawback of reducing the stiffness while increasing the positioning errors.

Each of the three kinematic chains connecting the bottom ring to the top demonstrates six degrees of freedom from its joints in the configuration shown. The first comes from the rotation of the sliding unit about the ring 14. The second comes from the rotation of the strut about the sliding unit 26 via yoke joint 202. The third comes from the extension of the strut via its prismatic joint. The final three come from the three degrees of rotation allowed for by the spherical or ball joint. To be defined as a parallel robot, the design must have the same number of actuators as it has degrees of freedom. As there are six degrees of freedom, there are six actuators: one prismatic (within the strut) and one rotational (between the sliding unit and the gear) for each of the three legs. Each actuator provides the upper ring with one degree of freedom. Alizade et al. (id.) have explored the range of motion in a setup such as this already, demonstrating the size of the assembly's workspace and analyzing both forward and rear displacement. They also declared that this assembly has a distinct advantage over the Steward/Gough platform in its ability to produce pure rotation.

The six degrees of freedom provided by these designs allow it the unique property of having a "virtual hinge." When repairing a deformed bone, it is essential that re-alignment takes place centered on the Center of Rotation of Angulation (CORA)—the point at which the proximal mechanical axis and distal mechanical axis intersect. In older systems (e.g. Ilizarov), it was essential to build a physical hinge into the assembly that aligned perfectly with the CORA. If a physician noticed halfway through the patient's treatment that the alignment of this hinge was off, it became necessary to physically repair the system and reposition the hinge. The virtual hinge afforded by six degrees of freedom greatly simplifies this process. No actual hinge must be installed initially; the two rings are able to generate rotation about any single line, forming the "virtual hinge" there. If a physician notices that the initially chosen line was inaccurate, all that must be done to fix the prescription is to simply correct the line acting as the virtual hinge. This can quickly and easily be done using software.

Figure 26:
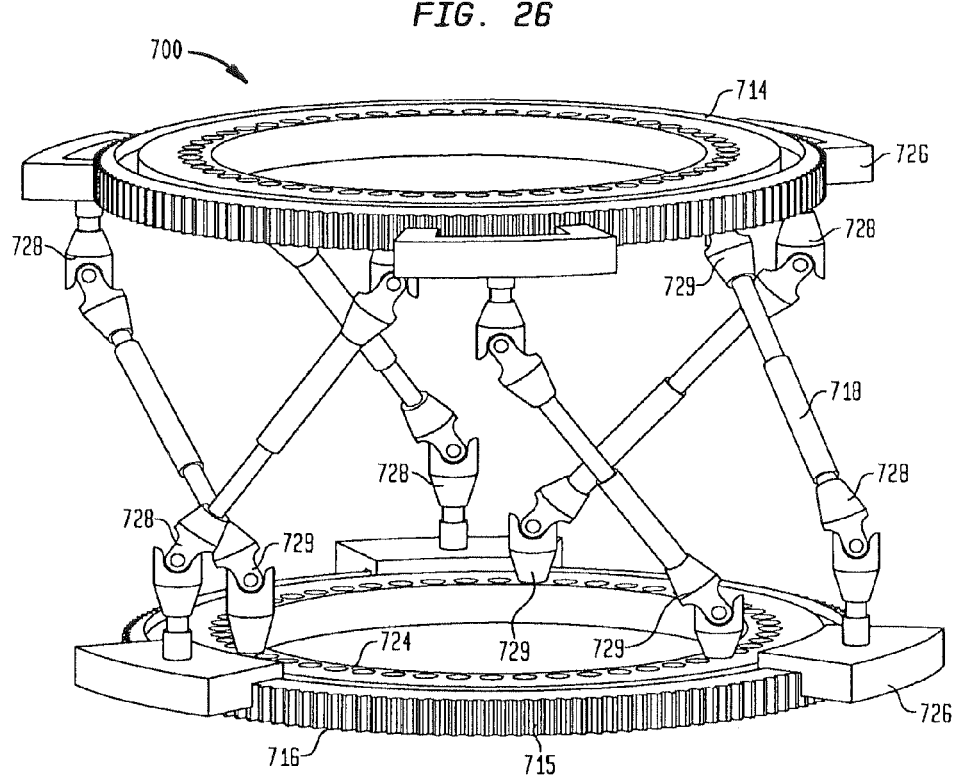
FIG. 26 is an isometric view of a six strut external fixation system according to an embodiment of the present disclosure.
Figure 27:
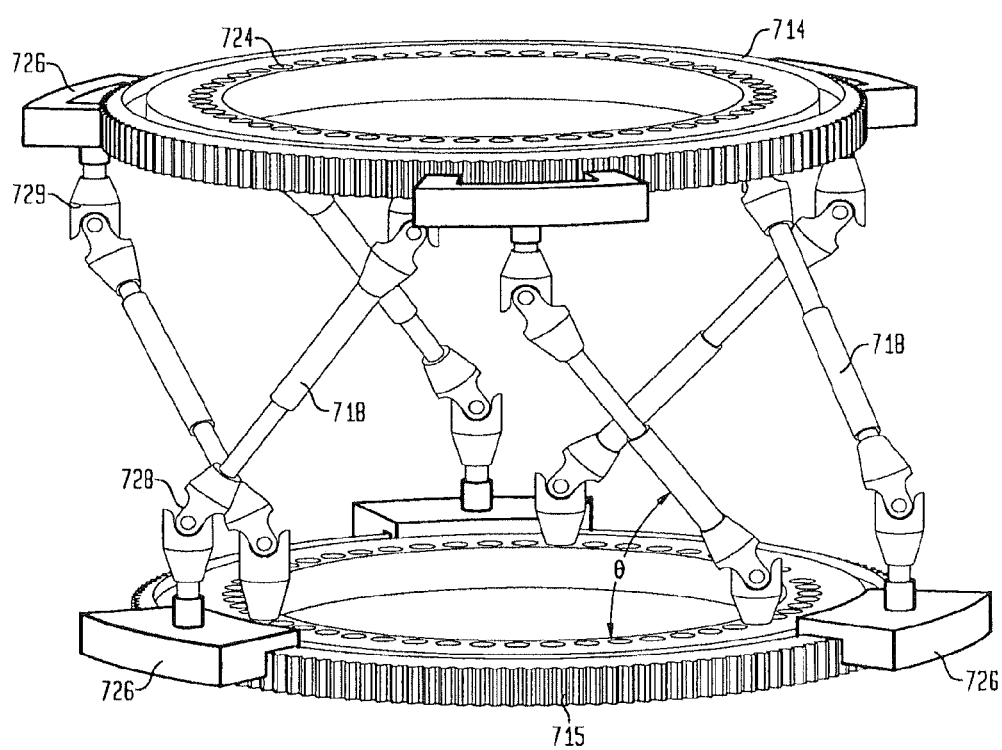
FIG. 27 is another isometric view of the six strut external fixation system shown in FIG. 1.

FIGS. 26 and 27 illustrate an embodiment of an external fixation system with six struts for manipulating the relative position of bone fragments to one another. The system is capable of moving in six axes of rotation. For movement, the system may incorporate either the use of the Stryker patented "smart tool" (U.S. Pat. No. 6,017,354) or six dedicated servo or stepper motors. The smart tool or servo/stepper motors are to be controlled by software. The software provides an interface for use by the surgeon or user to determine daily adjustments. The system also incorporates potentiometers or optical encoders (at the moving points along the frame) to not only determine the initial position (for software input/setup) but also to insure that the daily adjustments are being made properly.

Each of the six struts 718 has a proximal and distal end. At the proximal end, the strut is connected to a ring with a sliding unit 726. At its distal end, it is bolted to the opposing ring. The six sliding units 726 move about the perimeter of the rings 714, 716 to adjust the effective distance between the rings. Sliding in the direction that increases the angle $\theta$ (FIG. 27) between the frame and the strut increases the distance between the rings. Sliding in the opposite direction decreases the distance.

Figure 29:
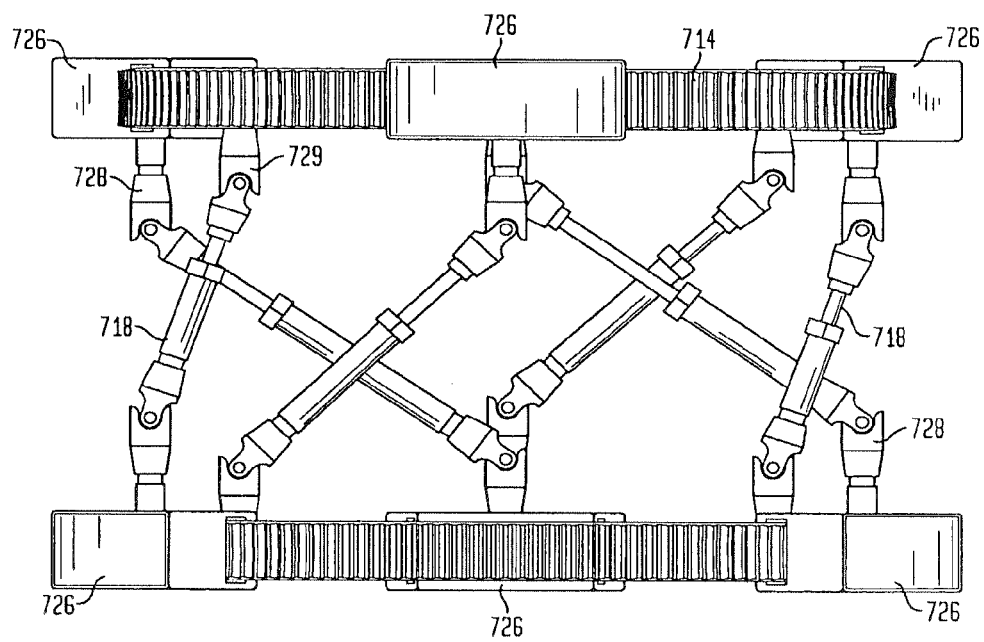
FIG. 29 is a side view of the external fixation system shown in FIG. 26.

When the external fixation system 700 is being set up in surgery, the struts' length can be changed to attain the optimal starting position (Optimal Position, see FIG. 29). This is important because there are certain positions where the struts 718 can interfere with one another, thus limiting the amount of movement possible before strut interference. Once the setup is complete and correction may begin, the struts are locked and the length is fixed. The shuttle units 726 then moved about the rings 714, 716 to adjust the ring's relative position in six axes of adjustment. When the rings 714, 716 are being moved by the system, the length of the strut 718 is constant and does not adjust.

When the struts are all equal length and each sliding unit's distal end is closest to the proximal end of its neighboring strut (see FIG. 28), the two rings 714, 716 are positioned parallel and vertically inline (see FIG. 29.)

Figure 28:
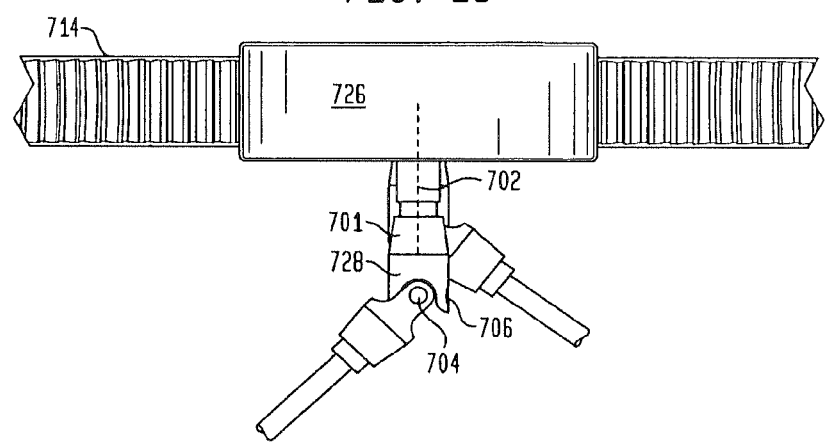
FIG. 28 is a side view of a shuttle unit connected to an upper ring.

Whenever the initial configuration of the struts 718 is such that the distal end of each strut is closest to the proximal end of its neighboring strut, see FIG. 28, it allows for the most optimal starting point and will be referred to as the "optimal position." From this position the frame is ideally situated to be able to make corrections before strut interference occurs.

Strut interference occurs when one strut's position prohibits another strut from moving past. This effectively limits the range of motion. By setting up the system 700 in the optimal position, one limits the effects interference has on the range of motion, thus maximizing the possible adjustments from the starting point.

Figure 30:
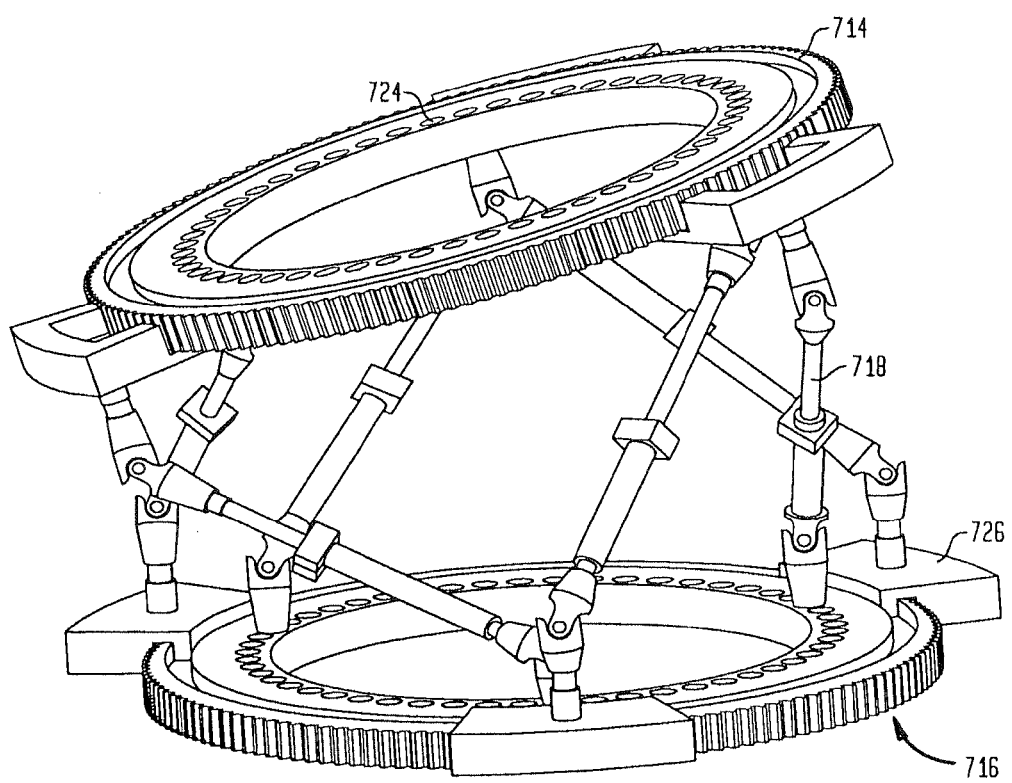
FIG. 30 is an isometric view of the external fixation system of FIG. 26, showing the lower and upper rings oriented in a first angular position.

In many cases the rings 714, 716 will not be parallel and inline immediately following surgery. If the struts were all the same length and the rings 714, 716 were not parallel, one could not achieve the optimal position of the struts. It is for this reason that the struts must be adjustable in length. Ideally, the system 700 will be positioned in the optimal position regardless of the relative position of one ring 714, 716 to another. As can be seen in FIG. 30, the strut lengths are different and the rings 714, 716 are not parallel or vertically inline but each sliding unit's distal end to be closest to the proximal end of its neighboring strut (optimal position). Before the correction is to begin in FIG. 30, the struts' lengths will be locked. To start the correction the software will determine the necessary movement of the shuttles units 726 to achieve proper alignment. Then, the sliding units or shuttles 726 move accordingly adjusting the position of the rings 714, 716 until the deformity is corrected.

Alternatively, different length struts could be provided that "snap" in to the system. This would allow the surgeon to get close to the optimal position. As one decreases the iterative different in length of the struts available, the probability of exactly attaining the optimal position increases. As a corollary, this increases the number of struts that are to be offered in a kit and the complexity of the setup. Allowing for an adjustable length strut would reduce the number of struts required in a kit to six. It is important to note that the adjustable length does not in any way control the movement of the rings. Once the struts' lengths are set intraoperatively (while installing the frame), they are fixed for the entirety of the frame's movement. This is inherently different than prior art spatial frames because they require the struts to adjust length to make any movement. With the present design, a user could adjust the struts 418 to the appropriate length before they were put on the frame, fix the lengths and install them into the frame. This would insure that no strut length adjusting occurred while struts were on the frame.

The length of the struts needed is dependent on the initial position of the system 700. For example, if the system 700 is set up such that the rings 714, 716 are parallel and vertically inline (See FIGS. 29 and 31), then all the struts 718 will be the same length. However, the distance between the rings 714, 716 dictates the required length of each strut 718 to achieve the optimal position. In cases where the rings 714, 716 are not parallel and vertically inline (See FIG. 30), the length of the struts 418 is to be adjusted so the system 700 starts in the optimal position. The following is a detailed description of the system.

FIGS. 26 and 27 illustrate an embodiment of a six strut external fixation system generally denoted as 700. External fixation system 700 includes an upper ring 714 and a lower ring 716. Each ring 714, 716 includes a plurality of circumferentially extending teeth 715 and a plurality of bores 724 adjacent the inner diameter of the ring. The external fixation system 700 includes a plurality of struts 718, which can be initially extended and then locked at a fixed length. Three struts 718 are connected at a first end to a shuttle or sliding unit 726 on ring 714 by a universal joint 728 and at a second end to one of the holes 724 in ring 716 via a universal joint 729. The other three struts 718 are connected to shuttle units 726 on ring 716 at one end by a universal joint 728 and by a second universal joint 729 to a hole 724 on ring 714.

FIG. 28 shows a sliding unit or shuttle 726 mounted on ring 714 and a universal joint 728. Universal joint 728 is connected to shuttle unit 726 and includes a yoke 701, which may be rotated about an axis 702 and two pin axis 704 and 706 respectively. In lieu of shuttle unit 726, external fixation system 700 may alternatively incorporate the shuttle units 26 depicted in FIG. 2 or any other shuttle unit or mechanism suitable for moving along the perimeter of a ring 714 or 716.

Figure 31:
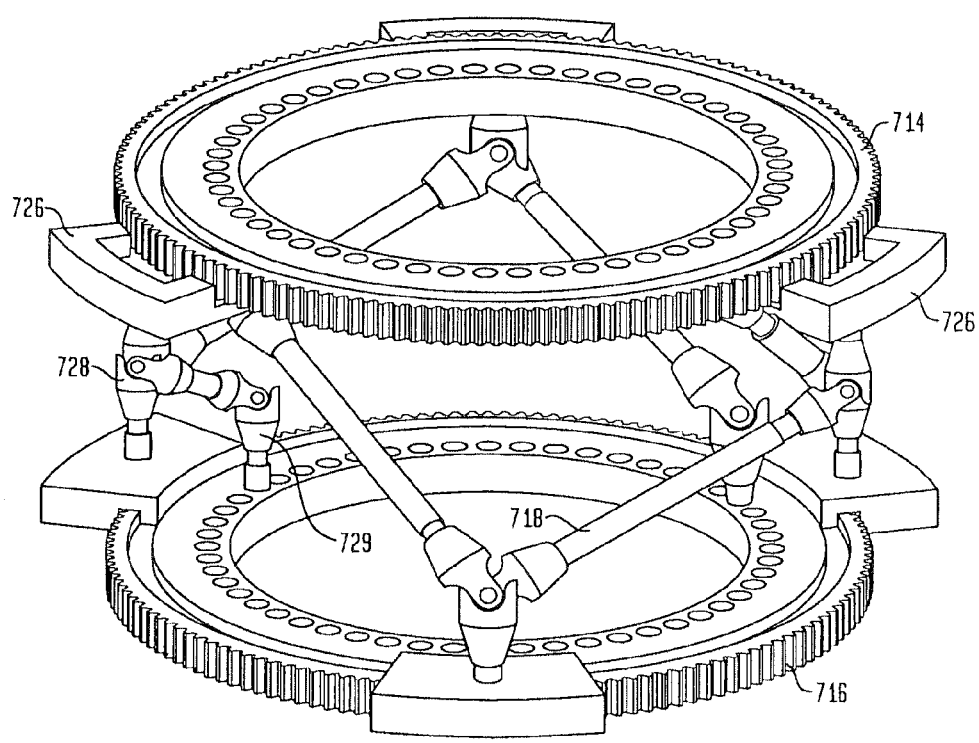
FIG. 31 is an isometric view of the external fixation with the lower and upper rings oriented substantially parallel to each other.

FIG. 29 shows rings 714 and 716 with three shuttles 726 mounted on each ring and six struts 718 respectively connected at a first end to a shuttle unit 726 and at a second end to a hole 724 on the opposite ring. Referring to FIG. 30, rings 714 and 716 are oriented at an angle to one another with the six struts 718 coupled at a first end to a shuttle 726 on a first ring 714 or 716 and a second end to one of the holes 724 on the other of the rings 714 or 716. As seen in FIG. 31, rings 714 and 716 can be adjusted to a parallel orientation with respect to each other. Such adjustment can be achieved either by adjusting the initial length of each strut 718 and then manipulating the location of the six shuttles 726 on their respective rings while maintaining the strut length fixed during the manipulation. Of course, if the manipulation is the initial set-up, the struts 718 may be adjusted in length to ensure that the rings 714, 716 are properly located with respect to a fractured long bone. Then movement of shuttle 726 will accomplish, over time, the desired correction.

Figure 32:
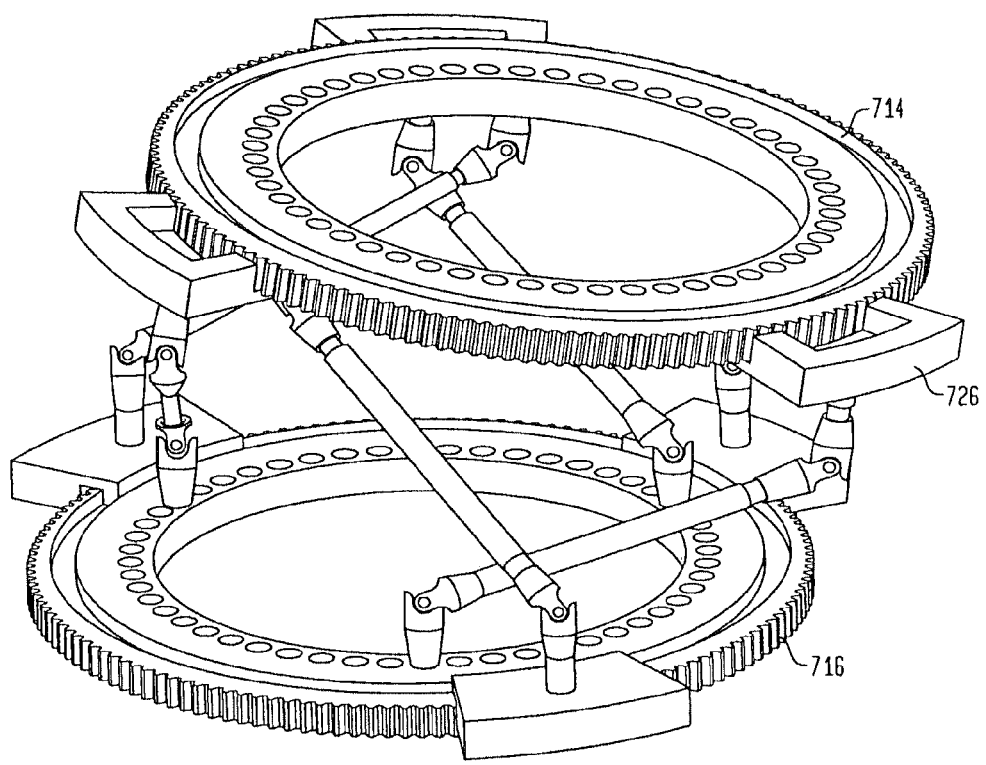
FIG. 32 is an isometric view of the external fixation system of FIG. 26 with the lower and upper rings oriented in a second angular position.

As shown in FIG. 32, rings 714 and 716 can be located in a second angular position. To place rings 714 and 716 in the second angular position, the respective shuttle units 726 are moved on the rings 714 or 716 in a controlled manner. Again, the alignment can initially be set by adjusting the strut length. The location of the shuttle unit 726 on a ring 714 or 716 can be controlled with a worm gear mechanism, as shown in FIG. 4F. Each shuttle unit 726 may contain a worm gear mechanism or any other suitable drive mechanism for facilitating movement of the shuttle unit 726 along a ring 714 or 716. The drive mechanisms are coupled to a computer-controlled stepper or servo motors. External fixation system 700 further includes a controller or any other suitable means for implementing the various inputs to the stepper or servo motors. The controller includes a microprocessor capable of manipulating data according to a mathematical equation describing the movement and/or position of the rings 714, 716.

The following mathematical expressions describe the movement and position of rings 714 and 716. This mathematical representation of a six strut platform is described by the position of one platform relative to the other.

Figure 33:
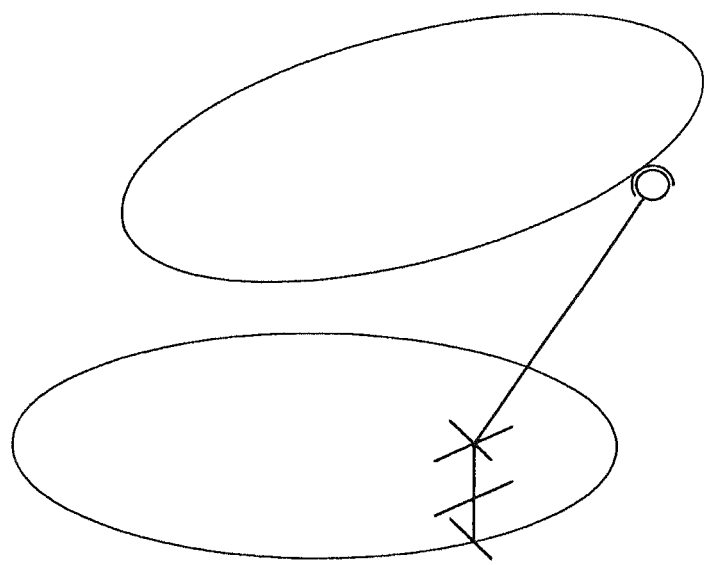
FIG. 33 is a schematic diagram of a six (6) degrees of freedom external fixation system with RRUS kinematic chains, wherein "R" stands for revolute join, "U" stands for universal joint, and "S" stands for spherical joint.
Figure 34:
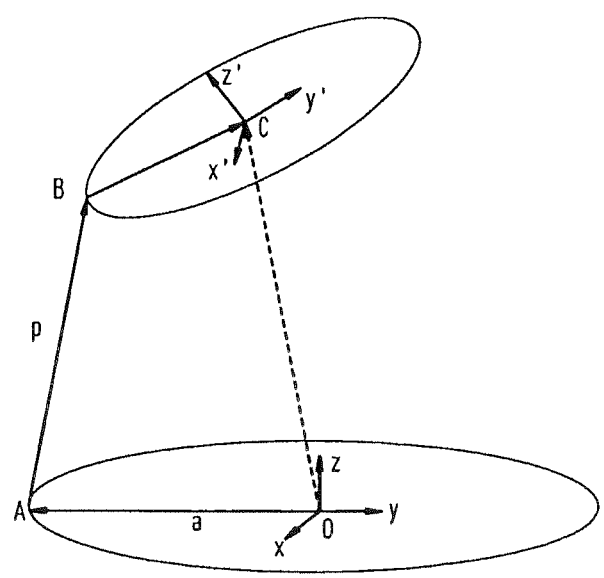
FIG. 34 is a vector model diagram of a six strut external fixation system, showing centers O and C.

FIG. 33 shows one of the six kinematic chains connected to a base and a moving platform in the proposed parallel robot configuration. Each platform is a ring with a known radius. Each kinematic chain has an endpoint on the base and moving platform. The endpoints' positions about the perimeter of each platform are measurable and therefore known. As seen in FIG. 34, the center points shall be described as point (center of base with radius a) and point C (center of moving ring with radius b). As the strut is connected to the base and moving platform the position can be defined in a cartesian coordinate system. Point A is described in the coordinate system of the base, which is (x,y,z) and point B is described in the coordinate system of the moving platform which is (x',y',z'). The struts' lengths are known and the distance between A and B is further described as p.

The rotation of the moving platform relative to the base platform can be expressed as the rotation of the (x',y',z')-coordinate system relative to the origin coordinate-system (x,y,z). The angles for the rotation are set to $(\Psi, \Phi, \Theta)$.

The vector $\overrightarrow{OC}$ describes the position of the center of the moving platform relative to the base platform and is represented by $$\overrightarrow{OC} = \overrightarrow{OA} + \overrightarrow{AB} + \overrightarrow{BC} \qquad (1)$$

This equals to $$\|\overrightarrow{OC}\| = \|\overrightarrow{OA} + \overrightarrow{AB} + \overrightarrow{BC}\| \qquad (2)$$

Equation (2) squared delivers an equation in which most of the components can be replaced by known variables.

$$\|\overrightarrow{OC}\|^2 = \|\overrightarrow{OA}\|^2 + \|\overrightarrow{AB}\|^2 + \|\overrightarrow{BC}\|^2 + 2(\|\overrightarrow{OA}\|\|\overrightarrow{AB}\| + \|\overrightarrow{AB}\|\|\overrightarrow{BC}\| + \|\overrightarrow{BC}\|\|\overrightarrow{OA}\|) \qquad (3)$$

With $\|\vec{AB}\|=\rho$ and $\|\vec{OA}\|=\alpha$

The vector $\vec{BC}$ is described in the origin base coordinate system and equals its description in the rotated coordinate system x',y',z' when it's multiplied with the rotation matrix R.

$$(\vec{BC})_{(x,y,z)} = R(\vec{BC})_{(x',y',z')} \quad (4)$$

The rotation matrix rotates each axis with the according angle ($\Psi, \Phi, \Theta$).

$$R = [R_z(\Psi) \cdot R_y(\Theta) \cdot R_x(\Phi)] \quad (5)$$

This results in the following rotation matrix:

$$R = \begin{bmatrix} \cos\theta\cos\psi & \sin\theta\sin\phi\cos\psi + \cos\phi\sin\psi & -\cos\phi\sin\theta\cos\psi + \sin\psi \\ -\cos\theta\cos\psi & -\sin\theta\sin\phi\cos\psi + \cos\phi\sin\psi & \cos\phi\sin\theta\cos\psi + \sin\psi \\ \sin\theta & -\sin\phi\cos\theta & \cos\phi\cos\theta \end{bmatrix} \quad (6)$$

Substituting all known variables into equation (3) gives us:

$$\|\vec{OC}\|^2 = \alpha^2 + \rho^2 + \|\vec{BC}\| + 2[\alpha\rho + \rho(R\vec{BC}) + \alpha(R\vec{BC})] \quad (7)$$

Given six unique struts, we have six unknowns: (x',y',z') which are coordinates of the point C and ($\Psi, \Phi, \Theta$) which are the angles of rotation of the normal to the circle with the center C. Equation (7) would give us 6 equations for the 6 unknowns from which the location of C can be calculated. Center C and radius b can be used to describe the position of the moving platform relative to the base platform.

Figure 35:
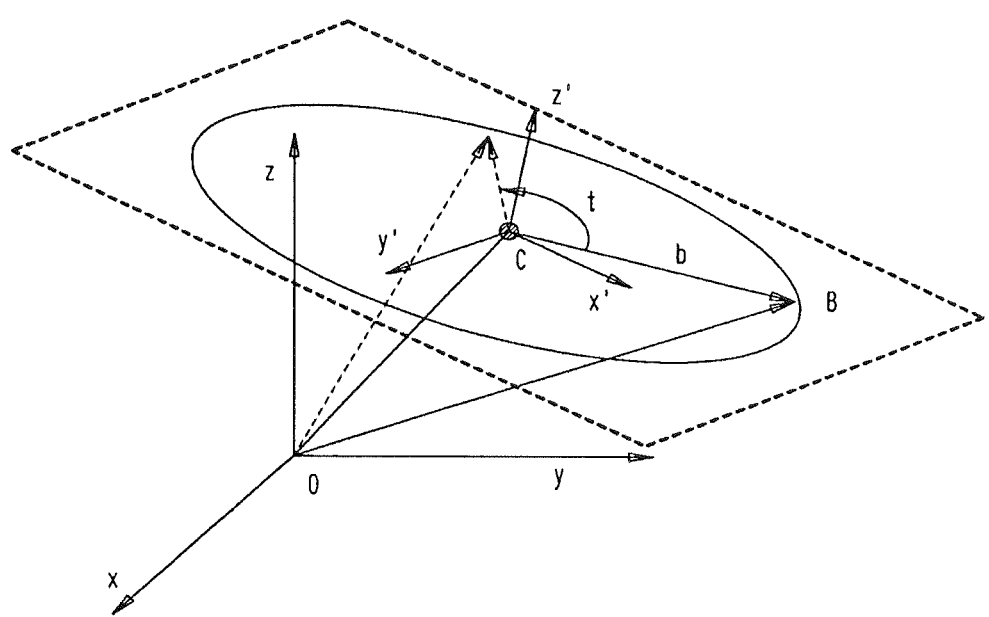
FIG. 35 is a vectorial model of a circle in Cartesian coordinate system.

With reference to FIG. 35, the description of the ring of the moving platform with respect to the center C of the base platform is a vector connecting Point O and point.

$$\vec{OB} = \vec{OC} + \vec{CB} \quad (8)$$

With the known rotation of the coordinate system, the circle lies in a plane spanned by the x'- and y'-axes. The normal to this plane is the z'-axes. The radius b rotates around this normal with the angle t. Therefore the circle is described by equation (9):

$$\vec{OB}(t) = \vec{OC} + b\cos(t)x' + b\sin(t)y' \quad (9)$$

Using the rotation matrix derived from the equations above, we get the equation for a ring with respect to the origin coordinate system (x,y,z):

$$\vec{OB}(t) = \vec{OC} + b\cos(t)Rx + b\sin(t)Ry \quad (10)$$

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
a first platform having at least a circular portion;
a second platform;
a plurality of non-prismatic kinematic chains having a first end connected to the first platform and a second end connected to the second platform, each kinematic chain including:
a first revolute joint;
a second revolute joint, the first and second revolute joints respectively rotatable about first and second perpendicular axes together forming a universal joint;
a third revolute joint mounted on the first platform and connected to the first revolute joint and adapted to revolve around a circumference of the circular portion of the first platform;
a spherical joint coupled to the second platform; and
means for rotating the second revolute joint about the second axis of the universal joint and for moving the third revolute joint along the first platform.

2. The external fixation system as set forth in claim 1, wherein the plurality of non-prismatic kinematic chains are fewer than six.

3. The external fixation system as set forth in claim 1 further comprising means for controlling a position of the kinematic chains relative to the second platform.

4. The external fixation system as set forth in claim 1, wherein the first platform includes a groove extending therealong, the groove being adapted to guide the movement of the third revolute joint along the first platform.

5. The external fixation system as set forth in claim 1, wherein the third revolute joint is configured to snap onto the first platform.

6. The external fixation system as set forth in claim 1, wherein the universal joint has a plurality of markings indicating angulation.

7. The external fixation system as set forth in claim 1, wherein the third revolute joint is configured to be driven.

8. The external fixation system as set forth in claim 1, wherein the third revolute joint includes a worm gear drive system for controlling the movement of the third revolute joint along the circumference of the circular portion of the first platform.

9. The external fixation system as set forth in claim 1 further comprising a means for controlling the position of the first platform with respect to the second platform by actuating the second and third revolute joints.

10. The external fixation system as set forth in claim 1, wherein second revolute joint of the universal joint includes a worm gear drive system for controlling articulation of the universal joint with respect to the third revolute joint mounted on the first platform.

11. An external fixation system comprising:
a first platform;
a second platform;
at least three non-prismatic kinematic chains each connecting the first platform to the second platform, each kinematic chain including at least two actuated joints, at least one actuated joint being configured to move along a perimeter of the first platform;
means for actuating the at least two actuated joints;
wherein each of the non-prismatic kinematic chains includes at least first, second and third revolute joints and a spherical joint.

12. The external fixation system as set forth in claim 11 wherein the first revolute joint of each kinematic chain is connected to the first platform and the second revolute joint of each kinematic chain is connected to the first revolute joint of each kinematic chain.

13. The external fixation system as set forth in claim 11 wherein the first revolute joint of each kinematic chain is connected to the first platform and the spherical joint of each kinematic chain is connected to the second platform.

14. The external fixation system as forth in claim 13 wherein the first revolute joint of each kinematic chain is configured to be driven.

15. The external fixation system as set forth in claim 11 wherein the second revolute joint forms part of a universal joint.

16. The external fixation system as set forth in claim 11 wherein the second and third revolute joints each define an axis of rotation and wherein the axes of rotation of the second and third revolute joints are oriented orthogonally with respect to each other.

17. The external fixation system as set forth in claim 11 wherein the second and third revolute joints form a universal joint.

18. The external fixation system as set forth in claim 11 further comprising means for controlling the position of each revolute joint relative to the first platform.

19. The external fixation system as set forth in claim 11 wherein the first platform has a planar configuration and defines a first plane and wherein the first revolute joint is configured to revolve around a longitudinal axis extending through the first plane of the first platform.

20. An external fixation system comprising:
first and second ring elements, the first ring element including a gear track around a circumference thereof;
three shuttles mounted on the first ring element for controlled movement about a circumference of the first ring element each shuttle having a first connector including a joint having first and second connected parts respectively rotatable about first and second perpendicular axes, and the system having three second connectors fixed to the second ring, the three shuttles having a gear engaging the gear track on the first ring;
three struts each having first ends connected to a respective shuttle by a first connector and a second end connected to a respective second connector, the second connector having a spherical joint freely rotatable with respect to the second ring element; and
drive means for controlling the movement of each shuttle about the circumference of the first ring and for controlling the movement of each strut first end about the second axis of the first connector.

21. The external fixation system of claim 20 wherein the drive means for controlling the position of the shuttle comprises a computer controlled drive motor for rotating the shuttle gear.

22. The external fixation system as set forth in claim 21 wherein the first part of the first connector is coupled to a respective shuttle and the second part of the first connector is coupled to a respective strut, the second part of the first connector is rotated about the second axis by a gear system driven by a computer controlled drive gear mounted on the first part of the first connector.

23. An external fixation system comprising:
first and second planar at least part-circular ring elements, centers of the first and second ring elements spaced along an axis, the first ring element having a circumferential gear track extending along a part-circular circumference thereof;
three and only three struts each having a longitudinal axis, each strut having a first and second end, the first end of each strut coupled to the first ring by a first connector and the second end of each strut coupled to the second ring by a second connector;
the second connector at the second end of each strut being a spherical joint allowing free rotation of the second end of each strut with respect to its longitudinal axis;
the first connector including first and second connected parts respectively rotatable about first and second perpendicular axes, a shuttle mounted on the track of the first ring for movement therealong and on the first part of the first connector, the strut first end connected to the second part of the first connector allowing rotation of the first end of each strut about the first and second perpendicular axes the shuttle having a gear engaging the gear track on the first ring; and
drive means for controlling the angular position of each strut first end about the second axis and drive means for rotating the shuttle gear for controlling the position of each shuttle along the circumferential gear track on the first ring.

24. The external fixation system of claim 23 wherein the drive means for controlling the position of the shuttle comprises a computer controlled drive motor for rotating the shuttle gear.

25. The external fixation system as set forth in claim 24 wherein the first part of the first connector is coupled to a respective shuttle and the second part of the first connector is coupled to a respective strut, the second part of the first connector is rotated about the second axis by a gear system driven by a computer controlled drive gear mounted on the first part of the first connector.

\* \* \* \* \*